United States Patent
Yared et al.

(10) Patent No.: US 8,600,511 B2
(45) Date of Patent: Dec. 3, 2013

(54) DEVICES AND METHODS FOR TREATMENT OF HEART FAILURE AND ASSOCIATED CONDITIONS

(71) Applicant: CVRx, Inc., Minneapolis, MN (US)

(72) Inventors: Nadim Yared, Medina, MN (US);
Dimitrios Georgakopoulos, Maple Grove, MN (US); Eric Grant Lovett, Mendota Heights, MN (US)

(73) Assignee: CVRx, Inc., Minneapolis, MN (US)

( * ) Notice: Subject to any disclaimer, the term of this patent is extended or adjusted under 35 U.S.C. 154(b) by 0 days.

(21) Appl. No.: 13/645,122

(22) Filed: Oct. 4, 2012

(65) Prior Publication Data
US 2013/0030309 A1 Jan. 31, 2013

Related U.S. Application Data

(63) Continuation of application No. 12/986,077, filed on Jan. 6, 2011, now Pat. No. 8,321,024, which is a continuation-in-part of application No. 12/485,895, filed on Jun. 16, 2009, now Pat. No. 8,326,430.

(60) Provisional application No. 61/061,938, filed on Jun. 16, 2008.

(51) Int. Cl.
*A61N 1/36* (2006.01)

(52) U.S. Cl.
USPC .......................................................... 607/44

(58) Field of Classification Search
USPC .......................................................... 607/44
See application file for complete search history.

(56) References Cited

U.S. PATENT DOCUMENTS

| | | | |
|---|---|---|---|
| 5,707,400 A | 1/1998 | Terry, Jr. et al. | |
| 5,800,468 A * | 9/1998 | Holmstrom | 607/17 |
| 6,115,633 A | 9/2000 | Lang et al. | |
| 6,522,926 B1 | 2/2003 | Kieval et al. | |
| 6,985,774 B2 | 1/2006 | Kieval et al. | |
| 7,580,746 B2 | 8/2009 | Gilkerson et al. | |

(Continued)

FOREIGN PATENT DOCUMENTS

| | | |
|---|---|---|
| WO | WO 2004/075928 A2 | 9/2004 |
| WO | WO 2006/031902 A2 | 3/2006 |
| WO | WO 2007/136851 A2 | 11/2007 |

OTHER PUBLICATIONS

U.S. Appl. No. 12/485,895, filed Jun. 16, 2009; Dimitrios Georgakopoulos et al.

(Continued)

*Primary Examiner* — Carl H Layno
*Assistant Examiner* — Paula J Stice
(74) *Attorney, Agent, or Firm* — Patterson Thuente Pedersen, P.A.

(57) ABSTRACT

Devices and methods of use are described for identification, treatment, and/or management of heart failure and/or associated conditions. An exemplary system may include a baroreflex activation device configured to be implantable proximate a blood vessel of a patient, a measurement device configured to be implantable proximate a blood vessel, and a control system coupled to the baroreflex activation device and the measurement device and in communication with a blood pressure sensing means. The control system is programmed to automatically determine pressure waveform data from the measurement device over a time period of at least a portion of one cardiac cycle, determine a patient physiological parameter based on the pressure waveform data, and compare the patient physiological parameter to a blood pressure measurement taken from the blood pressure sensing means.

29 Claims, 18 Drawing Sheets

(56) References Cited

U.S. PATENT DOCUMENTS

| | | | |
|---|---|---|---|
| 7,643,875 B2 | 1/2010 | Heil, Jr. | |
| 7,647,114 B2 | 1/2010 | Libbus | |
| 7,873,413 B2 * | 1/2011 | McCabe et al. | 607/9 |
| 8,116,873 B2 | 2/2012 | Anderson et al. | |
| 8,321,024 B2 | 11/2012 | Georgakopoulos et al. | |
| 8,326,430 B2 | 12/2012 | Gerogakopoulos et al. | |
| 8,401,652 B2 | 3/2013 | Georgakopoulos et al. | |
| 2002/0058877 A1 * | 5/2002 | Baumann et al. | 600/485 |
| 2002/0151816 A1 | 10/2002 | Rich et al. | |
| 2003/0149450 A1 * | 8/2003 | Mayberg | 607/3 |
| 2004/0102712 A1 | 5/2004 | Belaleazar et al. | |
| 2004/0176672 A1 | 9/2004 | Silver et al. | |
| 2004/0220632 A1 | 11/2004 | Burnes | |
| 2005/0143779 A1 | 6/2005 | Libbus | |
| 2005/0154418 A1 | 7/2005 | Kieval et al. | |
| 2005/0251033 A1 | 11/2005 | Scarantino et al. | |
| 2005/0251212 A1 | 11/2005 | Kieval et al. | |
| 2006/0004417 A1 | 1/2006 | Rossing et al. | |
| 2006/0047218 A1 | 3/2006 | Bloom et al. | |
| 2006/0074453 A1 | 4/2006 | Kieval et al. | |
| 2006/0089678 A1 * | 4/2006 | Shalev | 607/23 |
| 2006/0094967 A1 | 5/2006 | Bennett et al. | |
| 2006/0282145 A1 * | 12/2006 | Caparso et al. | 607/118 |
| 2006/0293712 A1 | 12/2006 | Kieval et al. | |
| 2007/0021792 A1 * | 1/2007 | Kieval et al. | 607/23 |
| 2007/0156061 A1 | 7/2007 | Hess | |
| 2009/0036777 A1 | 2/2009 | Zhang et al. | |
| 2009/0132002 A1 | 5/2009 | Kieval | |
| 2009/0143837 A1 | 6/2009 | Rossing et al. | |
| 2009/0198302 A1 | 8/2009 | Anderson et al. | |
| 2010/0004714 A1 | 1/2010 | Georgakopoulos et al. | |
| 2012/0095523 A1 | 4/2012 | Yared et al. | |
| 2012/0123506 A1 | 5/2012 | Gerogakopoulos et al. | |
| 2012/0149998 A1 | 6/2012 | Anderson et al. | |

OTHER PUBLICATIONS

U.S. Appl. No. 12/986,077, filed Jan. 6, 2011, Nadim Yared et al.

U.S. Appl. No. 13/360,339, filed Jan. 27, 2012. Dimitrios Georgakopoulos et al.

International Search Report and Written Opinion; PCT/US2012/020516; Jun. 25, 2012; 12 pages.

Application and File History for U.S. Appl. No. 13/646,824, filed Oct. 8, 2012. Inventors: Georgakopoulos et al.

Application and File history for U.S. Appl. No. 13/691,484, filed Nov. 30, 2012. Inventors: Georgakopoulos et al.

* cited by examiner

Fig. 6

EJECTION DURATION $\quad ED(msec) = T_i - T_f$

HEART RATE $\quad HR(BEATS/MIN) = 60/T_T$

PRESSURE AT FIRST SHOULDER $\quad P_1(mm\ Hg) = P[T_1]$

PRESSURE AT SECOND SHOULDER $\quad P_2(mm\ Hg) = P[T_2]$

PRESSURE AT DIASTOLE $\quad P_d(mm\ Hg) = P[T_f]$

PRESSURE AT SYSTOLE $\quad P_3(mm\ Hg) = P[T_p]$

PRESSURE AT END-SYSTOLE $\quad P_{ES}(mm\ Hg) = P[T_i]$

AUGMENTED PRESSURE $\quad AP(mm\ Hg) = P_2 - P_1$

MEAN DIASTOLIC PRESSURE $\quad MDP(mm\ Hg) = \dfrac{\sum\limits_{i=T_i}^{T_i} P_i}{T_T - T_i}$ MEAN ARTERIAL PRESSURE $\quad MAP(mm\ Hg) = \dfrac{\sum\limits_{i=T_f}^{T_T} P_i}{T_T}$ MEAN SYSTOLIC PRESSURE $\quad MSP(mm\ Hg) = \dfrac{\sum\limits_{i=T_f}^{T_f} P_i}{T_i - T_f}$ AUGMENTATION INDEX $\quad AI(\%) = 100 \times \dfrac{P_2 - P_d}{P_1 - P_d}$ TENSION TIME INDEX $\quad TTI(mm\ Hg \cdot BEATS/MIN) = HR \times MSP \times (T_i - T_f)$ DIASTOLIC TIME INDEX $\quad DTI(mm\ Hg \cdot BEATS/MIN) = HR \times MDP \times (T_T - T_i)$

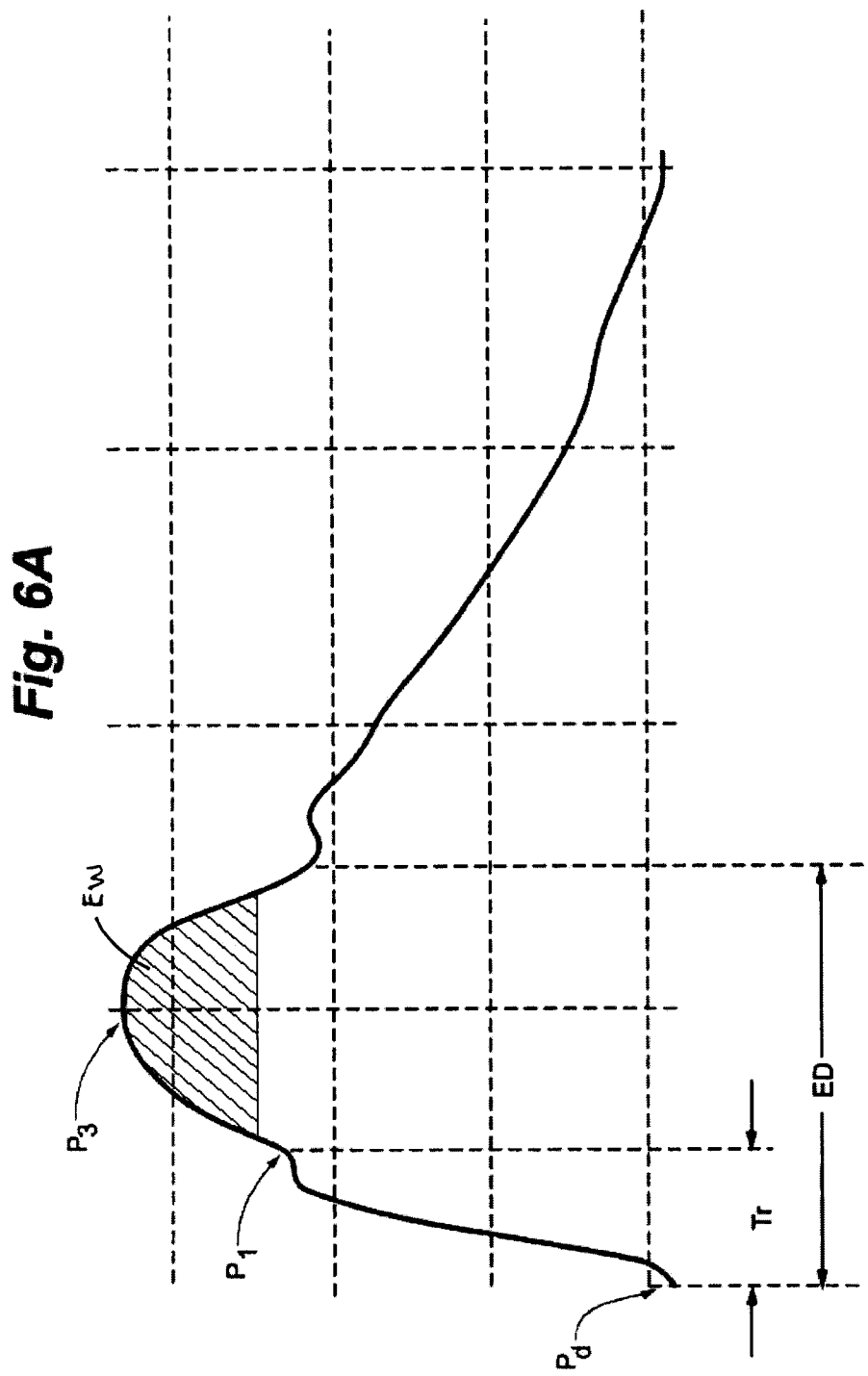

AUGMENTATION INDEX

Fig. 8A

| N = 19 | BASELINE | Δ 3 MONTHS | Δ 12 MONTHS |
|---|---|---|---|
| OFFICE CUFF SYSTOLIC BP (mmHg) | 179.4 ± 24.2 | -22.8 ± 25.8‡ | -27.0 ± 24.7‡ |
| OFFICE CUFF DIASTOLIC BP (mmHg) | 106.0 ± 17.6 | -12.3 ± 18.7* | -13.2 ± 19.9* |
| HEART RATE (bpm) | 72.9 ± 11.4 | -4.6 ± 10.1 | -2.6 ± 8.6 |
| SEPTAL WALL THICKNESS (mm) | 14.0 ± 3.2 | -1.0 ± 1.2‡ | -1.7 ± 1.9‡ |
| LV POSTERIOR WALL THICKNESS (mm) | 13.4 ± 2.4 | -0.8 ± 0.9‡ | -1.5 ± 1.1‡ |
| LV MASS (g) | 288 ± 80.7 | -33.8 ± 30.8‡ | -55.8 ± 43.7‡ |
| LV MASS INDEX (g/m$^2$) | 132.4 ± 32.4 | -15.5 ± 13.3‡ | -26.0 ± 18.2‡ |
| RELATIVE WALL THICKNESS | 0.54 ± 0.12 | -0.02 ± 0.05 | -0.05 ± 0.06† |
| ANTIHYPERTENSIVE MEDICATIONS (#) | 5.2 ± 1.9 | -0.3 ± 1.8 | -0.5 ± 0.8* |

Fig. 8B

| CHANGE IN CARDIAC STRUCTURE, BP, HEART RATE AND MEDICATION | | | |
|---|---|---|---|
| | BASELINE (N=32) | Δ 3 MONTHS (N=32) | Δ 12 MONTHS (N=19) |
| LVOT DIAMETER (mm) | 19.59±1.92 | +0.59±1.13* | +0.74±1.05* |
| LVMI (g/m2) | 138.8±36.0 | -17.9±16.3‡ | -26.0±18.2‡ |
| PULSE PRESSURE (mmHg) | 74.9±16.2 | -11.4±18.1‡ | -14.3±12.3‡ |
| SYSTOLIC BP (mmHg) | 179.8±24.9 | -22.8±30.5‡ | -27.8±25.1‡ |
| DIASTOLIC BP (mmHg) | 105.0±17.4 | -11.4±19.7† | -13.5±20.4* |
| HEART RATE (bpm) | 72.5±10.5 | -4.9±9.0† | -3.2±8.3 |
| ANTI-HTN MEDICATIONS (#) | 5.2±1.7 | -0.3±1.5 | -0.5±0.8* |
| VALUES: MEAN±SD  *p≤0.01  †p<0.005  ‡p≤0.001 | | | |

Fig. 8C

| N=21 | BASELINE | Δ 4 MONTHS | Δ 13 MONTHS |
|---|---|---|---|
| ARTERIAL COMPLIANCE (mL/mmHg) | 1.12 ± 0.40 | 0.16 ± 0.34 | 0.21 ± 0.37 |
| EJECTION FRACTION | 64.6 ± 5.1 | 1.9 ± 2.6 | 1.9 ± 6.8 |
| IVS THICKNESS AT END DIASTOLE | 14.0 ± 3.1 | -1.0 ± 1.1 | -1.6 ± 1.9 |
| eMVO2 (mmHg*BPM) | 12788 ± 2617 | -1958 ± 2771 | -2210 ± 2635 |
| eMVO2/60 | 213.1 ± 43.6 | -32.6 ± 46.2 | -36.8 ± 43.9 |

|  | BASELINE | BAT |
|---|---|---|
| HR | 72 | 52 |
| SAP | 102 | 84 |
| MAP | 81 | 58 |
| EDP | 10.5 | 8.1 |
| dpdt | 2215 | 2000 |
| PTI | 24.5 | 19.4 |
| CENTRAL PP | 40 | 48 |
| Abd PP | 47 | 40 |
| Ao dpdt | 1420 | 1700 |

| PARAMETER (N=3) | % CHANGE BASELINE |
|---|---|
| HEART RATE | -15+3 |
| SYSTOLIC PRESSURE | -26.5±5 |
| LV DIASTOLIC PRESSURE | -41±3.3 |
| LV DIASTOLIC VOLUME | 1.2±0.5 |
| EJECTION FRACTION | 28±10 |
| STROKE VOLUME | 31±10 |
| CARDIAC OUTPUT | 12±6 |
| RESISTANCE | -40±7 |
| TAU | -15±5 |
| PEAK FILLING RATE | 14±6 |
| RPP | -25±4 |

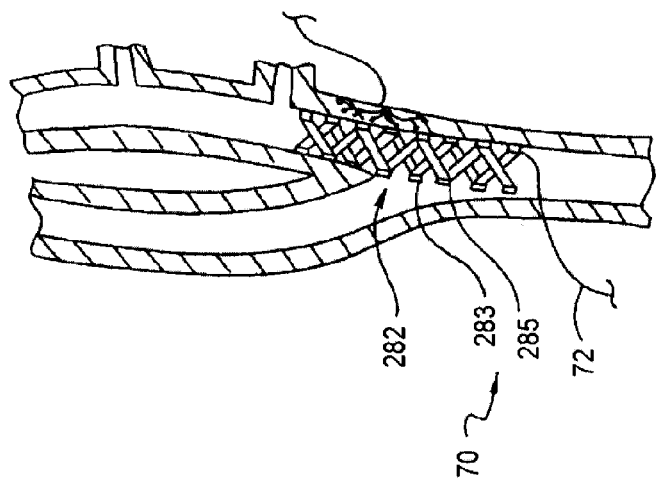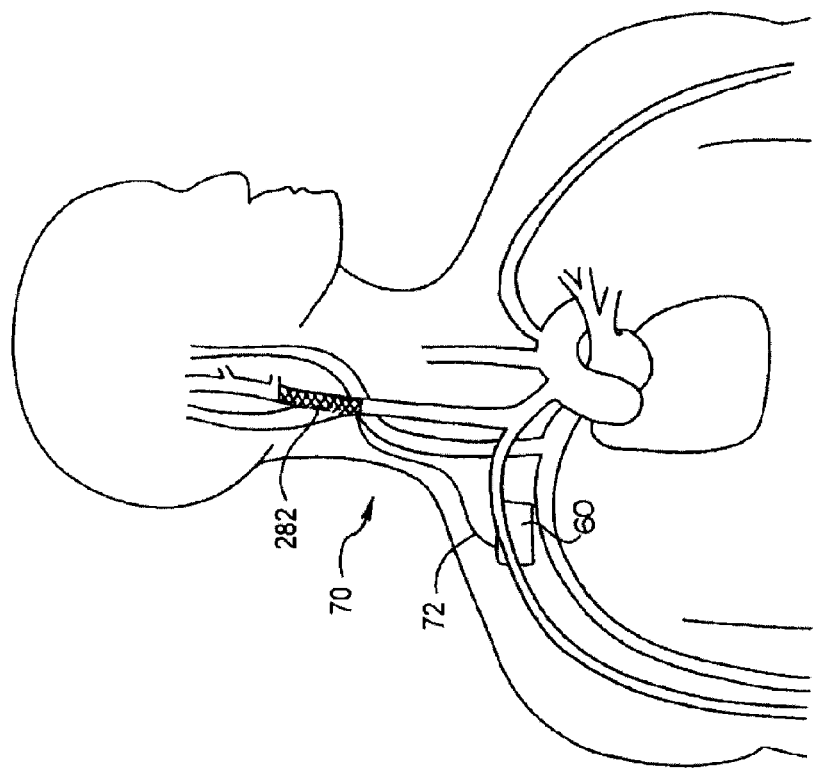
Fig. 16A
Fig. 16B

DEVICES AND METHODS FOR TREATMENT OF HEART FAILURE AND ASSOCIATED CONDITIONS

RELATED APPLICATIONS

This application is a continuation of U.S. patent application Ser. No. 12/986,077, filed Jan. 6, 2011 and now issued as U.S. Pat. No. 8,321,024, which is a continuation-in-part of U.S. patent application Ser. No. 12/485,895, filed Jun. 16, 2009 and now issued as U.S. Pat. No. 8,326,430, which claims the benefit of U.S. Provisional Application No. 61/061,938 filed Jun. 16, 2008, the disclosures of which are hereby incorporated by reference in their entireties.

FIELD OF THE INVENTION

The present invention relates generally to medical devices and methods of use for the treatment and/or management of heart failure and associated conditions, and more specifically to devices and methods for controlling the baroreflex system for the treatment, diagnosis and/or management of heart failure and associated conditions and their underlying causes.

BACKGROUND OF THE INVENTION

Hypertension, or high blood pressure, is a major cardiovascular disorder that is estimated to affect over 50 million people in the United Sates alone, and is a leading cause of heart failure and stroke. It is the primary cause of death in over 42,000 patients per year and is listed as a primary or contributing cause of death in over 200,000 patients per year in the United States alone. Hypertension occurs in part when the body's smaller blood vessels (arterioles) constrict, causing an increase in blood pressure. Because the blood vessels constrict, the heart must work harder to maintain blood flow at the higher pressures. Sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke.

Sustained high blood pressure may eventually result in an enlarged and damaged heart (hypertrophy), which may lead to heart failure. Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year.

Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state.

Heart failure can be generally classified into two categories: systolic and diastolic heart failure. The heart contracts and relaxes with each heartbeat—these phases are referred to as systole (the contraction phase) and diastole (the relaxation phase). Systolic heart failure (SHF) is characterized by low ejection fraction. In patients with diastolic heart failure (DHF), contraction may be normal but relaxation of the heart may be impaired. This impairment is generally caused by a stiffening of the ventricles. Such impairment is referred to as diastolic dysfunction and if severe enough to cause pulmonary congestion (increased pressure and fluid in the blood vessels of the lungs), diastolic heart failure. DHF patients differ from those patients with SHF, in that DHF patients may have a "normal" ejection fraction. However, because the ventricle doesn't relax normally, the pressure within the ventricle increases and the blood filling the ventricle exceeds what is "normal". People with certain types of cardiomyopathy may also have diastolic dysfunction.

Left ventricular hypertrophy refers to a thickening of the left ventricle as a result of increased left ventricular load. Left ventricular hypertrophy can be a significant marker for cardiovascular disorders and most common complications include arrhythmias, heart failure, ischemic heart disease, and sudden death. Although left ventricular hypertrophy (LVH) increases naturally with age, it is more common in people who have high blood pressure or have other heart problems. Because LVH usually develops in response to hypertension, current treatment and prevention mainly includes managing hypertension. Typical diagnosis involves the use of echocardiograms (ECHO) and electrocardiograms (ECG).

The SPHYGMOCOR system (AtCor) provides a non-invasive assessment of the cardiovascular system and autonomic function. The SPHYGMOCOR waveform provides physicians with clinically important information using a variety of cardiovascular parameters including augmentation index, augmentation pressure, central pulse pressure, central systolic pressure, and ejection duration. The SPHYGMOCOR system comprises a non-invasive pressure transducer that uses a radial artery (external wrist) measurement and BP monitor. It works by using the pressure probe to record the pressure wave at the radial artery, which is then calibrated with the brachial blood pressure. However, this system does not provide a direct measurement of pressure, and the system is not able to be used as an implanted, continuous system.

Vascular stiffness in aging and its relation to cardiovascular disease is an important topic of current research. Vascular stiffness has been proposed as a risk factor for overall cardiovascular morbidity and mortality because of its suggested role in elevated blood pressure, increased left ventricular mass and heart failure. Current therapies targeting vascular stiffness, therefore, include those prescribed for these conditions, such as hypertension drug therapy. Pulse pressure is a known, simple measurement that can be used as a surrogate to aortic stiffness. Additionally, wave reflections can be inferred from detailed computer-aided pulse wave contour analysis, such as with the AtCor SPHYGMOCOR system.

Heart failure is known to be a multi-organ disease and there is recent evidence that the gut (including the splanchnic circulation) plays an important role in cardiac diseases. The circulatory system of humans includes the pulmonary circulation and the systemic circulation. The pulmonary circulation ensures deoxygenated blood is returned to the lungs and oxygenated blood returned to the heart, while the systemic circulation ensures that oxygenated blood is supplied to the body. The systemic circulation includes the splanchnic circulation (or visceral circulation), which ensures that digestive organs receive blood through the vessels supplying the abdominal viscera. Acute decompensated heart failure or pulmonary congestion develops as a result of blood being redistributed from the splanchnic circulation to the pulmonary circulation, manifesting in fluid build-up in the chest and an inability of the patient to breathe. The specific mechanism of this transfer of fluids between the two is not yet fully understood.

The current standard of care for a patient exhibiting congestion is a variety of drugs, including diuretics, which causes excretion of fluid through the renal system. Splanchnic nerve stimulation has been described in the art to treat shock. For example, WO 2006/0031902 to Machado et. al teaches a method of treating hemodynamic derangement and controlling the mobilization of splanchnic circulation by stimulating the splanchnic nerve. Neither drug therapy, nor nerve stimulation therapy has been successful in providing a controlled therapy for congestive heart failure or acute decompensated heart failure.

A number of drug treatments have been proposed for the management of hypertension, heart failure, and other cardiovascular disorders. These include vasodilators to reduce the blood pressure and ease the workload of the heart, diuretics to reduce fluid overload, inhibitors and blocking agents of the body's neurohormonal responses, and other medicaments. Such medications can be effective for a short time, but cannot be used for expanded periods because of side effects. Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month.

Each of these approaches may be at least partly beneficial to patients, however, each of the therapies has its own disadvantages. For example, drug therapy is often incompletely effective. Drugs often have unwanted side effects and may need to be given in complex regimens. These and other factors contribute to poor patient compliance with medical therapy. Drug therapy may also be expensive, adding to the health care costs associated with these disorders. Likewise, surgical approaches are very costly, may be associated with significant patient morbidity and mortality and may not alter the natural history of the disease.

Accordingly, there continues to be a need for improved devices and methods for diagnosing, treating and/or managing high blood pressure, heart failure, and their associated cardiovascular and nervous system disorders.

SUMMARY OF THE INVENTION

Embodiments of the present invention comprise devices and methods of use for the diagnosis, treatment and/or management of heart failure and associated conditions. In one embodiment, the present invention comprises devices and methods for controlling the baroreflex system of a patient for the treatment and/or management of heart failure and associated conditions and their underlying causes.

In one embodiment, the present invention comprises methods and devices of sensing, measuring, and monitoring parameters indicative of cardiovascular function. In one embodiment, an impedance sensor is provided on, in or proximate a blood vessel to obtain waveform data of blood movement in the vessel. The obtained waveform data provides information relating to a forward wave and a reflected wave of a heart beat and also to the augmentation index. In another embodiment, the obtained waveform may be used to calculate parameters indicative of cardiovascular disorders and associated conditions, such as splanchnic circulation or left ventricular mass. In a further embodiment, the sensed waveform may be used to provide feedback in conjunction with a delivered therapy, such as a baroreflex therapy or a cardiac resynchronization therapy.

In one embodiment, the present invention comprises a method including providing a baroreflex therapy system including a blood pressure sensor and a heart rate sensor, providing an implantable measurement device proximate a blood vessel of a patient, the implantable measurement device including an electrode, providing a control system coupled to the baroreflex therapy system and the implantable measurement device, the control system programmed to automatically determine an impedance of the blood vessel with the implantable measurement device over a time period of at least one cardiac cycle, determine arterial stiffness of the blood vessel based on the impedance, determine blood pressure and heart rate, and activate, deactivate or otherwise modulate the baroreflex therapy system to deliver a baroreflex therapy based on the blood pressure, heart rate and arterial stiffness.

In one embodiment, the present invention comprises a system including an implantable baroreflex activation device, a blood pressure sensor, a heart rate sensor, an implantable measurement device configured to be implanted proximate a blood vessel of a patient, the implantable measurement device including an electrode, and a control system coupled to the baroreflex activation device, the blood pressure sensor, the heart rate sensor and the implantable measurement device, the control system programmed to automatically determine an impedance of the blood vessel with the implantable measurement device over a time period of at least one cardiac cycle, determine arterial stiffness of the blood vessel based on the impedance, determine blood pressure and heart rate, and activate, deactivate or otherwise modulate the baroreflex therapy system to deliver a baroreflex therapy based on the blood pressure, heart rate and arterial stiffness.

In one embodiment, the present invention comprises a method including providing a baroreflex therapy system, including a blood pressure sensor and a heart rate sensor, providing an implantable measurement device proximate a blood vessel of a patient, the implantable measurement device including an electrode, providing a control system coupled to the baroreflex therapy system and the implantable measurement device, and providing instructions recorded on a tangible medium for operating the control system to deliver a baroreflex therapy, the instructions comprising determining an impedance of the blood vessel with the implantable measurement device over a time period of at least one cardiac cycle, determining arterial stiffness of the blood vessel based on the impedance, determining blood pressure and heart rate, and activating, deactivating or otherwise modulating the baroreflex therapy system to deliver the baroreflex therapy based on the blood pressure, heart rate and arterial stiffness.

In one embodiment, the claimed invention comprises an implantable baroreflex system, comprising a baroreflex activation device configured to be implantable proximate a blood vessel of a patient, a measurement device configured to be implantable proximate a blood vessel, and a control system coupled to the baroreflex activation device and the measurement device, and in communication with a blood pressure sensing means. The control system is programmed to automatically determine pressure waveform data from the measurement device over a time period of at least a portion of one cardiac cycle, determine a patient physiological parameter based on the pressure waveform data, and compare the patient physiological parameter to a blood pressure measurement taken from the blood pressure sensing means.

In one embodiment, the claimed invention comprises a method, comprising causing a baroreflex therapy system to be manufactured and made available to a user, the baroreflex therapy system including a baroreflex activation device, a measurement device, and a control system coupled to the baroreflex activation device and the measurement device, causing a blood pressure sensing means to be manufactured and made available to a user, the blood pressure sensing means in communication with the control system, and providing instructions to the user recorded on a tangible medium. The instructions comprise implanting the activation device proximate a blood vessel of a patient, implanting the measurement device proximate a blood vessel, and causing the control system to determine pressure waveform data from the implantable measurement device over a time period of at least a portion of one cardiac cycle, determine a patient physiological parameter based on the pressure waveform data, obtain a blood pressure measurement via the blood pressure sensing means, and compare the blood pressure measurement to the patient physiological parameter.

In one embodiment, the claimed invention comprises a method, comprising providing an implantable baroreflex therapy system, including a baroreflex activation device, a measurement device, and a control system coupled to the baroreflex activation device and the measurement device, and providing a blood pressure sensing means in communication with the control system; and implanting the baroreflex therapy system such that the therapy electrode is proximate a blood vessel of a patient and the measurement electrode is proximate the blood vessel. The control system is programmed to determine an impedance of the blood vessel with the implantable measurement device over a time period of at least one cardiac cycle, determine a patient physiological parameter based on the impedance of the blood vessel, obtain a blood pressure measurement via the blood pressure sensing means, and compare the blood pressure measurement to the patient physiological parameter.

BRIEF DESCRIPTION OF THE DRAWINGS

The invention may be more completely understood in consideration of the following detailed description of various embodiments of the invention in connection with the accompanying drawings, in which:

FIG. 6 is a table of parameters that may be derived from the waveform of FIG. 5.

FIG. 6A illustrates additional information that can be derived from the central pressure waveform.

FIG. 8A is a table depicting patient physiological parameters following application of a baroreflex therapy according to an embodiment of the present invention.

FIG. 8B is a table depicting patient physiological parameters following application of a baroreflex therapy according to an embodiment of the present invention.

FIG. 8C is a table depicting patient physiological parameters following application of a baroreflex therapy according to an embodiment of the present invention.

FIGS. 16A and 16B are schematic illustrations of a baroreceptor activation device in the form of an internal bipolar conductive structure which electrically or thermally induces a baroreceptor signal in accordance with an embodiment of the present invention.

Figure 1B:
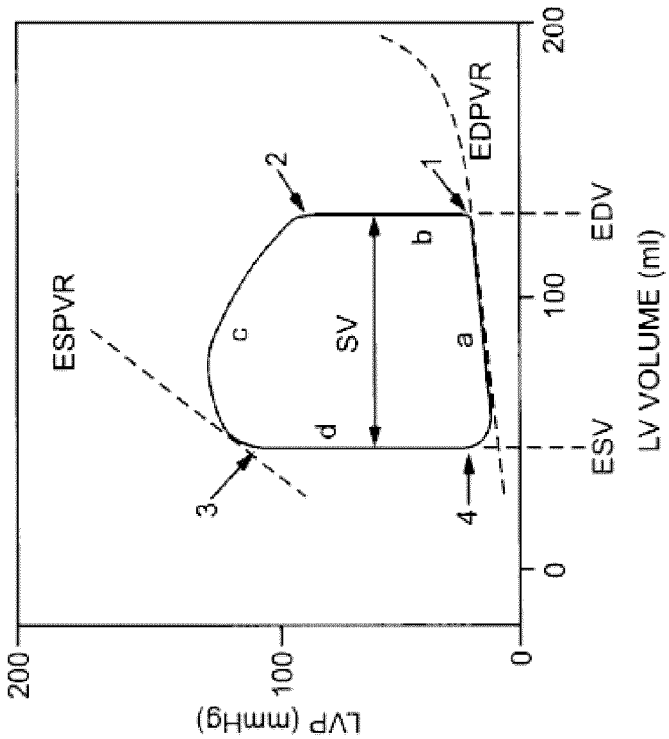
FIG. 1B is a graph of a PV loop.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Methods for treating heart failure and associated conditions in a subject typically comprise identifying a patient in need of treatment and stimulating a baroreflex with a baroreflex activation device to improve the symptoms and conditions associated with heart failure. In some variations, the baroreflex activation device is implanted proximate the baroreceptor, and in other variations, the baroreflex activation device is external. The stimulation provided by the baroreflex activation device may be any suitable stimulation. For example, it may be electrical stimulation, mechanical stimulation, thermal stimulation, chemical stimulation, or combinations thereof. In some variations the stimulation is electrical stimulation. The stimulation may be pulsed or continuous.

Figure 14:
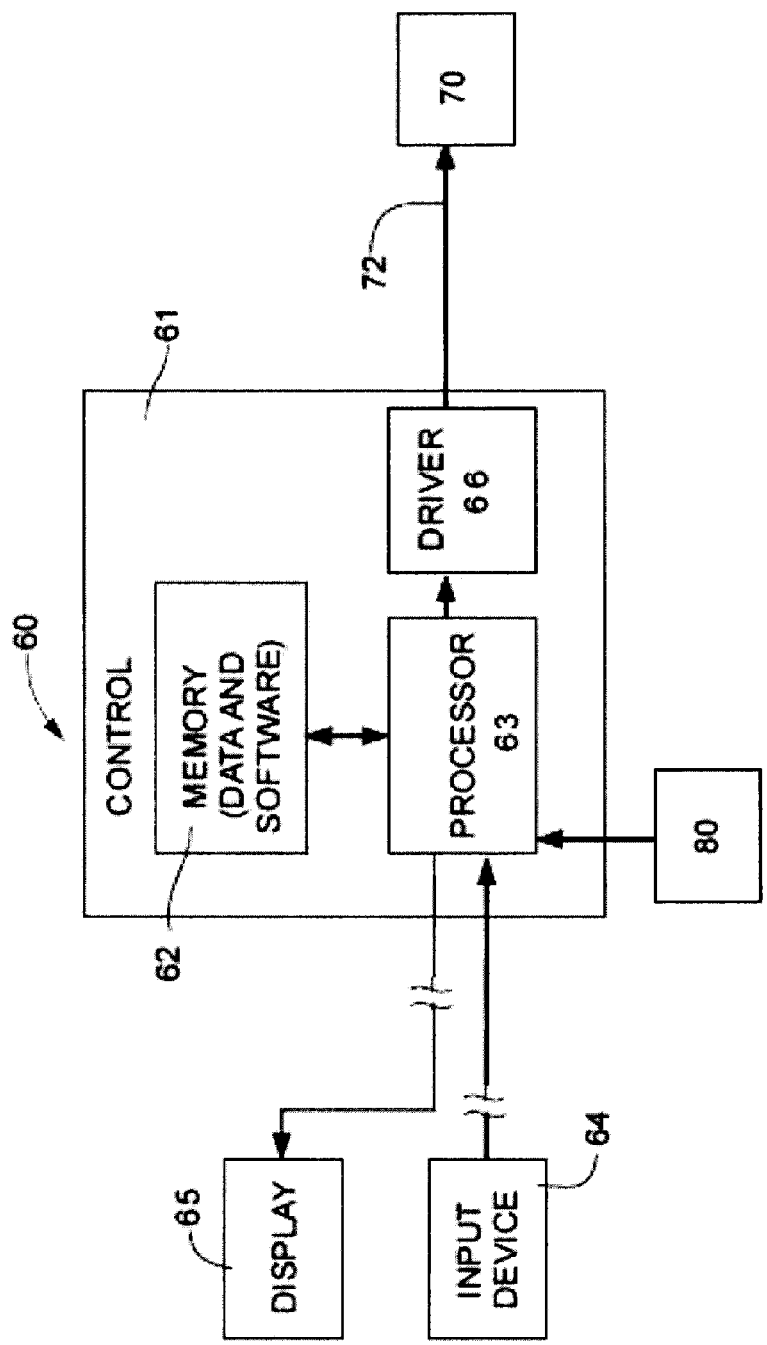
FIG. 14 is a schematic illustration of a baroreceptor activation system in accordance with the present invention.

With reference to FIG. 14, the present invention generally provides a system including a control system 60, a baroreceptor activation device 70, and a sensor 80 (optional), which generally operate in the following manner. The sensor 80 senses and/or monitors a parameter (e.g., cardiovascular function) indicative of the need to modify the baroreflex system and generates a signal indicative of the parameter. The control system 60 generates a control signal as a function of the received sensor signal. The control signal activates, deactivates or otherwise modulates the baroreceptor activation device 70. Typically, activation of the device 70 results in activation of the baroreceptors 30. Alternatively, deactivation or modulation of the baroreceptor activation device 70 may cause or modify activation of the baroreceptors 30. The baroreceptor activation device 70 may comprise a wide variety of devices which utilize mechanical, electrical, thermal, chemical, biological, or other means to activate baroreceptors 30. Thus, when the sensor 80 detects a parameter indicative of the need to modify the baroreflex system activity (e.g., excessive blood pressure), the control system 60 generates a control signal to modulate (e.g. activate) the baroreceptor activation device 70 thereby inducing a baroreceptor 30 signal that is perceived by the brain to be apparent excessive blood pressure. When the sensor 80 detects a parameter indicative of normal body function (e.g., normal blood pressure), the control system 60 generates a control signal to modulate (e.g., deactivate) the baroreceptor activation device 70.

All of the specific embodiments of the baroreceptor activation device 70 are suitable for implantation, and are preferably implanted using a minimally invasive percutaneous translumenal approach and/or a minimally invasive surgical approach, depending on whether the device 70 is disposed intravascularly, extravascularly or within the vascular wall 40. The baroreceptor activation device 70 may be positioned anywhere baroreceptors 30 affecting the baroreflex system 50 are numerous, such as in the heart, in the aortic arch, in the common carotid arteries near the carotid sinus, in the subclavian arteries, or in the brachiocephalic artery. The baroreceptor activation device 70 may be implanted such that the device 70 is positioned immediately adjacent the baroreceptors 30.

By way of example, the control system 60 includes a control block 61 comprising a processor 63 and a memory 62. Control system 60 is connected to the sensor 80 by way of sensor cable 82. Control system 60 is also connected to the baroreceptor activation device 70 by way of electric control cable 72. Thus, the control system 60 receives a sensor signal from the sensor 80 by way of sensor cable 82, and transmits a control signal to the baroreceptor activation device 70 by way of control cable 72.

The memory 62 may contain data related to the sensor signal, the control signal, and/or values and commands provided by the input device 64. The memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event.

The control system 60 may be implanted in whole or in part. For example, the entire control system 60 may be carried externally by the patient utilizing transdermal connections to the sensor lead 82 and the control lead 72. Alternatively, the control block 61 and driver 66 may be implanted with the input device 64 and display 65 carried externally by the patient utilizing transdermal connections therebetween. As a further alternative, the transdermal connections may be replaced by cooperating transmitters/receivers to remotely communicate between components of the control system 60 and/or the sensor 80 and baroreceptor activation device 70.

For additional information pertaining to cardiovascular anatomy and exemplary baroreceptor and baroreflex therapy systems, reference is made to the following patents and patent applications: Published Patent Application No. 2006/0004417 to Rossing et al., Published Patent Application No. 2006/0074453 to Kieval et al., Published U.S. Patent Application No. 200910143837 to Rossing et al., U.S. Pat. Nos. 6,522,926 to Kieval et al., 6,985,774 to Kieval et al., 7,480,532 to Kieval et al., 7,499,747 to Kieval et al., and 7,840,271 to Kieval et al., the disclosures of which are hereby incorporated by reference in their entireties.

In one embodiment, the invention provides a system and methods for obtaining a blood pressure waveform, and using the pressure waveform to derive parameters indicative of cardiovascular disorders. The waveform may be obtained independent of a therapy, such as for a stand-alone diagnostic and monitoring system, or the waveform may be used to provide feedback to a closed-loop therapy system. In such closed-loop system, one can use the waveform data to program, or adjust therapy to improve said cardiovascular disorders, and continuously monitor the status of the therapy in order to provide targeted, precise and controlled therapy.

Figure 15A:
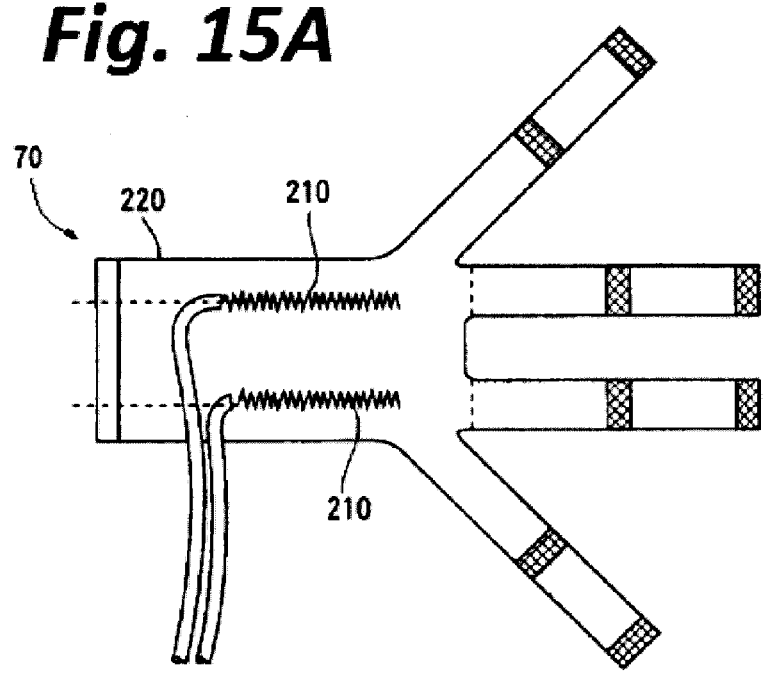
FIG. 15A is an embodiment of an extravascular measurement device according to an embodiment of the present invention.
Figure 15B:
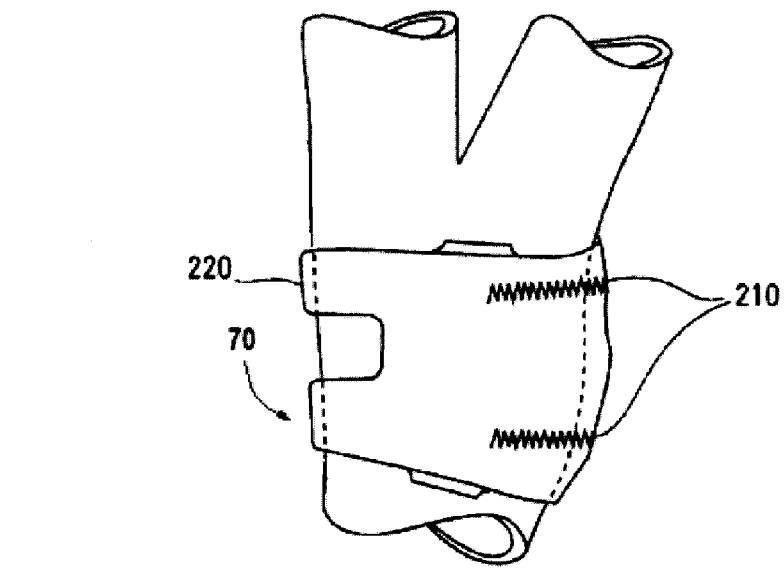
FIG. 15B is an embodiment of an extravascular measurement device implanted on a carotid artery according to one embodiment of the present invention.

The pressure waveform may be obtained with the use of electrodes positioned on, in or proximate a blood vessel, such as the carotid sinus or carotid artery. The electrodes measure impedance along or through the blood vessel. A number of patient physiologic parameters may be determined by measuring the electrical impedance of a blood vessel with the use of electrodes spaced along and/or across the wall of the blood vessel, as described in further detail in U.S. Pat. No. 8,116,873 to Anderson et al., the disclosure of which is incorporated by reference in its entirety. From the obtained impedance values, a waveform can be generated, such as in FIG. 5. The waveform may comprise a forward wave component and a reflected wave component. Suitable electrode arrangements for obtaining the waveform include an extravascular wrap having a plurality of electrodes positioned radially or longitudinally on the vessel as depicted in FIGS. 15A-15B, or an intravascular implant as depicted in FIGS. 16A-16B, or an intravascular device resembling an electrophysiology catheter, having at least a plurality of electrodes. Signals from the sensor can be measured continuously or on an appropriate basis to gather hemodynamic information for the patient.

The electrical impedance of the vessel can be determined by applying a measurement signal having a known, constant parameter and monitoring a resultant signal having a resultant parameter. The measurement signal may comprise an alternating current (AC) signal, or a direct current (DC) signal, such as a bi-phasic pulsed DC signal. In one embodiment, the known parameter of the measurement signal comprises a constant voltage, while the resultant parameter of the resultant signal comprises electric current. In another embodiment, the known parameter of the measurement signal comprises a constant current, while the resultant parameter comprises voltage.

The measurement signal can be transmitted through, and the monitored signal measured with, one or more implantable electrodes. The electrodes may be of the annular type, or unipolar point-type, or multi-polar, or other suitable type. In one embodiment depicted in FIG. 15A, two diagnostic electrodes 210 are provided on extravascular wrap 220, which is configured to wrap around at least a portion of a blood vessel. Referring to FIG. 15B, extravascular wrap 220 is implanted on common carotid artery 14, proximate the carotid sinus, such that electrodes 210 are longitudinally spaced from one other along the length of the blood vessel. In this embodiment, impedance is measured pervascularly, that is, along a length of a portion of the blood vessel. In an alternate embodiment not shown, electrodes 210 are spaced circumferentially around the vessel in the same plane. In an example of such an embodiment, the electrodes may be directly opposing one another such that the electrodes are spaced 180 degrees apart around the circumference of the vessel. The impedance is then measured transvascularly, that is, across at least part of the interior of the vessel. In a further embodiment, electrodes 210 may be spaced apart longitudinally as well as circumferentially on the blood vessel.

In another embodiment, two or more measurement electrodes are provided on or with an intravascular stent. Electrodes may be directly coupled to the intravascular stent, in which case the stent must be non-conductive, or measurement electrodes may be provided as part of an electrically insulative sleeve or wrap used in conjunction with the intravascular stent.

Various alternative embodiments are contemplated for the electrode structure, including its design, implanted location, and method of electrical activation. For example, electrode structure 282 may be bipolar using leads connected to either end of the structure 282 as shown in FIGS. 16A and 16B. In the embodiment of FIGS. 16A and 16B, electrode structure 282 includes two or more individual electrically conductive members 283/285 which are electrically isolated at their respective cross-over points utilizing insulative materials. Each of the members 283/285 is connected to a separate conductor contained within the electrical lead 284. Alternatively, an array of bipoles may be used, or as a further alternative, a multipolar arrangement may be used wherein three or more electrically conductive members are included in the structure 282. For example, a tripolar arrangement may be provided by one electrically conductive member having a polarity disposed between two electrically conductive members having the opposite polarity.

Referring now to another embodiment, the impedance measurement system may be combined with or used in conjunction with a baroreflex therapy device having dedicated stimulation electrodes. In one embodiment, two or more measurement electrodes are implanted on or about a blood vessel, and communicably coupled to a controller, preferably the same controller as utilized by baroreflex therapy device. In another embodiment, the measurement electrodes are coupled to the baroreflex therapy device.

In one embodiment, the stimulation electrodes of the therapy device may be configured to conduct impedance measurements as well as provide therapy, such that a delivered therapy signal acts as both the therapy source and the driving measurement source. The same electrodes are therefore used to transmit the therapy signal (which also functions as the measurement signal) and to monitor the resultant signal as therapy is being delivered. The measurement sampling rate is therefore the same as the therapy rate. The electrodes can be positioned as two laterally spaced annular rings around the blood vessel in or about which baroreflex modulation device is implanted, such as the carotid sinus. Alternatively, the electrodes can be spaced apart along the longitudinal axis of the blood vessel.

In one embodiment, the waveform data is used to determine the augmentation index, which is indicative of arterial stiffness. The system and methods of this embodiment increase venous reserve and capacitance, thereby improving vascular elasticity and vascular compliance with the majority of bodily vessels.

In one embodiment, the waveform data is indicative of LV mass and/or LV mass index. Referring to the waveform of FIG. 6A, the shaded area represents extra energy expenditure (Ew) imposed on the left ventricle during ejection. Referring still to FIG. 6A, Ew can be calculated as $2.09*(Ps-Pl)*(Ed-Tr)$, wherein Tr is the reflected wave time. This energy expenditure correlates with LV mass index, such that LV mass index can be monitored and logged with a waveform generated from an implanted transarterial impedance measurement device.

Well-known historical data on primary wave and augmentation index from a variety of sources demonstrated that reflected waves arrive earlier and central augmentation increases markedly with advancing age. Such data also supports speculation that central aortic stiffness and forward wave amplitude are the primary mechanism for increased central and peripheral systolic and pulse pressure with advancing age in healthy adults. It would be advantageous to reduce the amplitude of forward and reflected waves, as well as delay the reflected wave.

Figure 2:
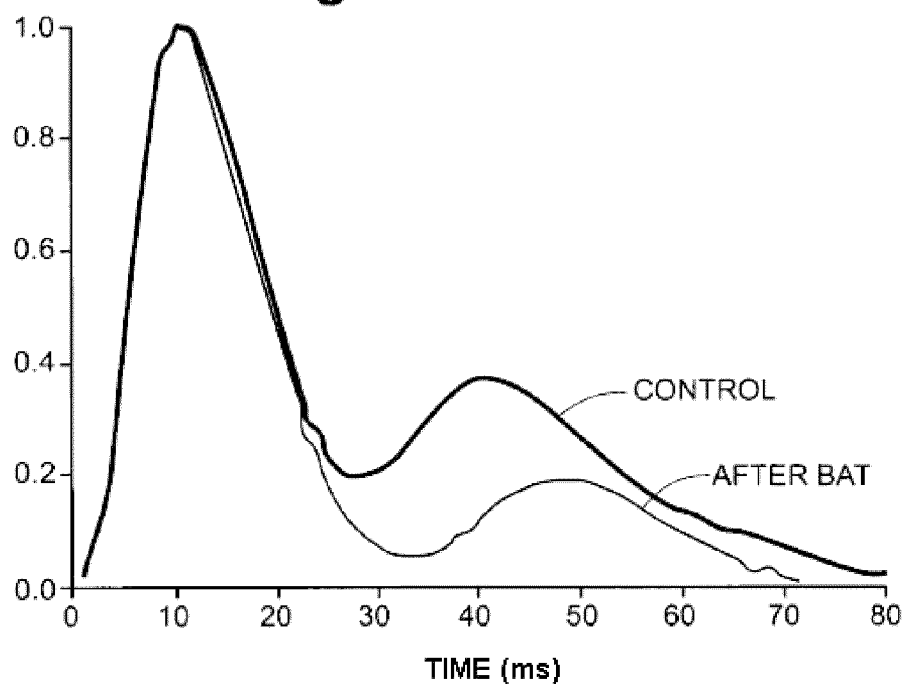
FIG. 2 is a graph depicting a reflected cardiac pressure wave before and after application of a baroreflex therapy to a canine according to an embodiment of the present invention.

To demonstrate the efficacy of the device and methods of the invention, experiments were performed on canines FIG. 2 depicts the reduction in amplitude of the reflected wave as well as the delay in time of the reflected wave. This data suggests a significant improvement in the vascular properties after delivery of a baroreflex activation therapy (BAT).

Figure 3:
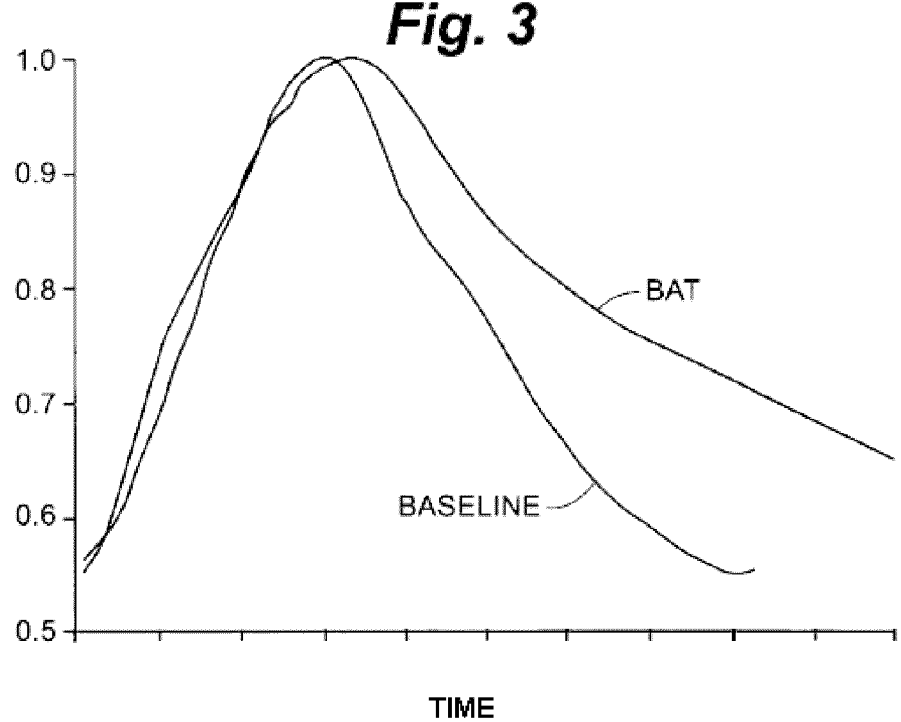
FIG. 3 is a graph depicting a reflected cardiac pressure wave before and after application of a baroreflex therapy to a human according to an embodiment of the present invention.

To demonstrate the efficacy of the present invention on human patients, studies were performed that measured the reflected wave before and after delivery of baroreflex activation therapy. FIG. 3 depicts the results illustrating the efficacy of baroreflex activation therapy in both reducing the amplitude of the reflected wave and delaying the time of the wave.

Figure 5:
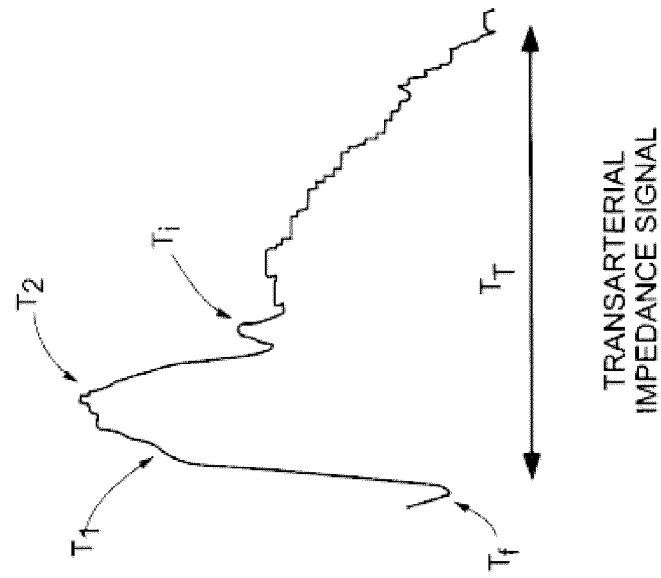
FIG. 5 is a central pressure waveform obtained by an embodiment of the present invention.
Figure 4:
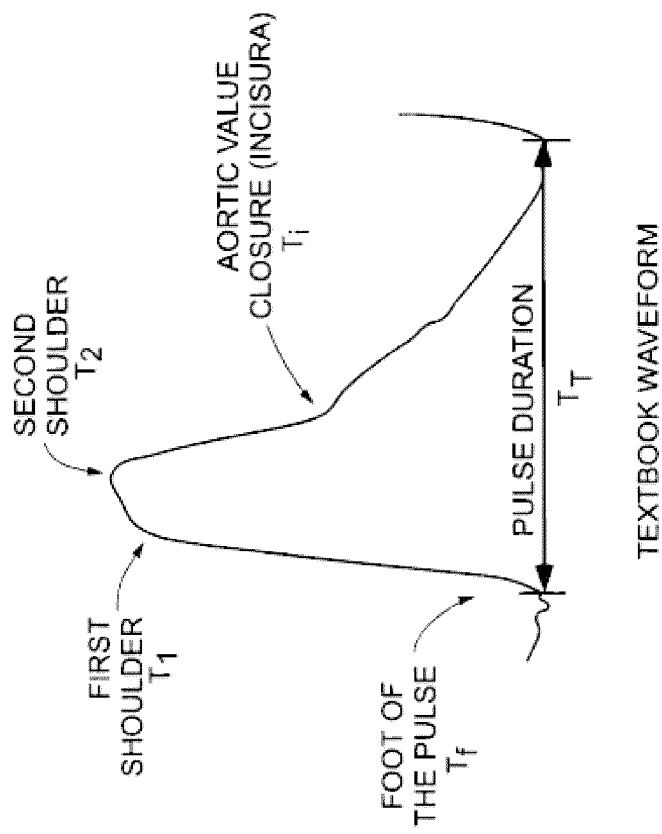
FIG. 4 is an example of a central pressure waveform.

It is possible to derive many parameters from a pressure waveform. FIG. 4. depicts a "textbook" pressure waveform, while FIG. 5 depicts a pressure waveform obtained by a transarterial impedance measurement according to embodiments of the present invention. Reference numerals are used consistently throughout FIGS. 4-6A unless otherwise noted. Many parameters obtainable from the pressure waveform are presented in FIG. 6. While the derivation of these parameters from a pressure waveform has previously been known, until now it has not been possible to obtain such a waveform from a chronically-implanted arrangement, allowing real-time monitoring of a patient.

In one embodiment, the processed signal is displayable on a computer monitor so as to be readable by a physician. The physician may select one or more of the indices of interest. Such indices may include those, for example, in FIG. 6. In one embodiment, pulse wave velocity is derived. In one embodiment, the invention provides algorithms and computer-readable media to automatically generate the parameters of interest. In one embodiment, the invention may provide automated feedback to the therapy device in order to adjust or modify therapy based on these waveform-derived indices.

Figure 7:
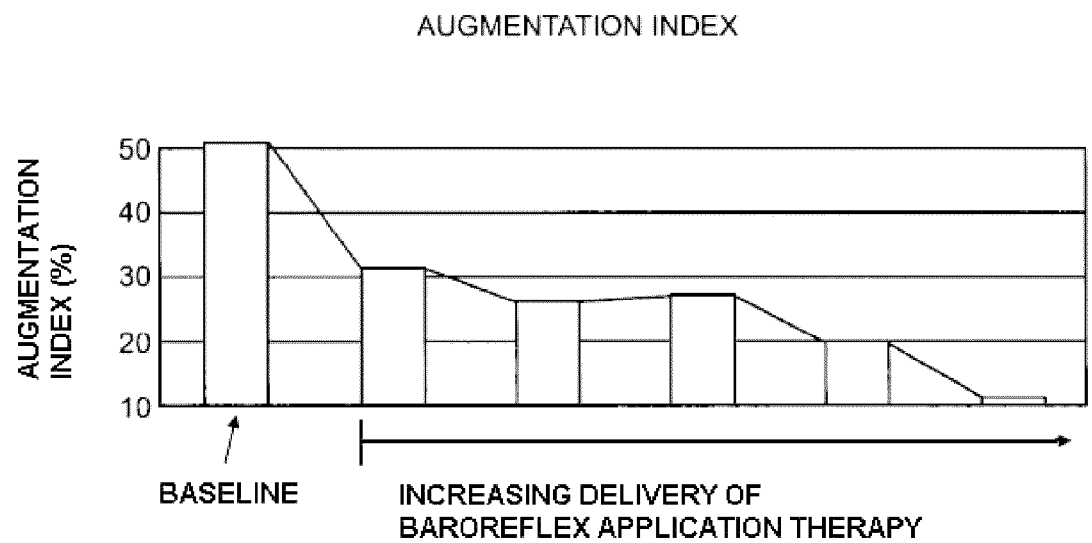
FIG. 7 is a chart depicting a reduction in augmentation index following application of a baroreflex therapy according to an embodiment of the present invention.

In one embodiment, the system derives augmentation index (AI) information and relies on the AI to adjust therapy. For example, if an AI is above a predetermined threshold level, baroreflex activation therapy is applied until the desired result (reduced AI) is achieved. In order to prove efficacy of baroreflex activation therapy in reducing AI in humans, an experiment was performed that delivered baroreflex activation therapy acutely to human implant patients. FIG. 7 depicts the results which conclude that AI was reduced when baroreflex activation therapy was delivered acutely in a human patient. Because AI is an indicator of arterial stiffness/compliance, this illustrates that baroreflex activation therapy affects arterial compliance, thereby reducing stiffness of vessels.

Benefits

Examination and analysis of pressure waveform data provides new insight to the effects of a baroreflex activation therapy. Embodiments of the invention have beneficial applications for diagnosing and managing heart failure and associated conditions. It has been observed experimentally that baroreflex activation therapy works by affecting a number of structures and function in the patient. Without limiting the scope of the invention, below is a list of observed benefits of the current invention and how each benefit may be measured or confirmed with the system of the invention.

One benefit is improved splanchnic circulation by way of increasing reservoir capacity of splanchnic circulation, resulting in net fluid transfer from lungs to gut. This fluid transfer may be measured by for example, trans thoracic impedance sensors that monitor fluid; other fluid sensors located for example in a vessel of the gut and a vessel of the pulmonary circulation; a sensor to measure elevated pulmonary artery pressure; monitoring weight gain; or monitoring incline during sleep.

Other benefits include reduced end diastolic pressure (EDP); increased cardiac output, measured by stroke volume and heart rate and by pulse contour methodology of the central pressure waveform; reduced diastolic stiffness, measured by −dp/dt, tau, edpvr; improved cardiac elasticity, measured by for example augmentation index; improved cardiac contractility, measured by arterial PV loop information derived from the central pressure waveform; +dp/dt, end systolic pressure-volume relationship (espvr); reduced likelihood that lone atrial fibrillation will occur; reduced likelihood that ventricular arrhythmias will occur; beneficial ventricular remodeling over time as evidenced by the changes in central pressure waveform; reduced detrimental remodeling that has previously occurred in the heart; reduced exercise intolerance as measured by patient activity with activity sensors; improved gut permeability; improved lung permeability; alleviation of fluid retention as measured by weight and other fluid sensors. Example embodiments of the present invention are described below.

Heart Failure

In one embodiment, sensors are used to monitor the fluids in a patient. Such sensors can be selected form a group consisting of edema sensors and other fluid/wetness sensors, chemical sensors, such as sensors to assay circulating plasma catecholamine, norepinephrine, angiotensin or BNP sensors, pressure sensors such as transarterial impedance, trans thoracic impedance, pulmonary artery or other intravascular pressure sensors and other pressure sensors. Such sensors can be located in a variety of locations including the heart, vessels, internal and external in order to measure parameters indicative of heart failure. Such sensors and methods of using them can be used as a stand alone system to monitor the build-up of fluids in the pulmonary circulation that is indicative of, for example heart failure. In another embodiment, such sensors can be used in a closed loop system with a therapy. In this embodiment, sensors monitor the presence or increase of fluids in the pulmonary circulation and provide baroreflex activation therapy. The sensors subsequently monitor the fluids in the splanchnic circulation and modulate therapy in order to move the fluids from pulmonary circulation to splanchnic circulation. Once the sensors sense the movement of fluids (that the pulmonary fluid has been reduced to an appropriate level), the therapy can be halted or adjusted to maintain the result. One could additionally use non-invasive methods to measure parameters conceived of by the inventions such as MRI and echocardiography.

In one embodiment, sensors are used to monitor the left ventricular mass of the patient in order to assess and monitor left ventricular hypertrophy. The methods of the invention could be used to treat patients exhibiting hypertrophy or as a monitor for ensuing hypertrophy in order to prevent it. Recent studies indicate that LVH was common at 1 year after heart transplantation, present in 83% of heart transplant recipients. Heart transplant recipients with severe LVH had significantly decreased survival. Therefore, the methods of the invention can be useful in the heart transplant population to monitor the development of hypertrophy and prevent it, thus improving outcomes for these patients. The sensors of the invention and methods of using them can be used as a stand alone system to monitor the LV mass, indicative of, for example left ventricular hypertrophy and heart failure or ensuing heart failure. In another embodiment, such sensors can be used in a closed loop system with a therapy. In this embodiment, sensors monitor the LV mass index in a patient and provide baroreflex activation therapy. The sensors subsequently monitor the LV mass and modulate therapy in order to reduce the LV mass. Once the sensors sense the reduction in LV mass, the therapy can be halted or adjusted to maintain the result.

To demonstrate efficacy of baroreflex activation therapy in human patients, experiments were performed to measure LV mass and related parameters. The experimental study results in FIGS. 8A and 8B using the LV Mass Index measurements and therapy methods of the invention show that baroreflex activation therapy reduced the following: blood pressure, LV wall thickness, LV mass, LV mass index (LVMI), and relative wall thickness.

Recent studies suggest that therapies which increase the diameter of the proximal aorta and left ventricular outflow tract (LVOT) may lower pulse pressure (PP) and thus may beneficially impact cardiovascular risk. As illustrated in FIG. 8B, baroreflex activation therapy increases LVOT diameter while reducing blood pressure, pulse pressure, and LVMI. Benefits are in addition to those achieved with intensive drug therapy.

In one embodiment, the present invention may reduce myocardial oxygen consumption (MVO2). MVO2 refers to the amount of oxygen consumed (or required) by the heart muscle for a contraction, and is increased under conditions such as in a heart failure patient, when heart rate is increased, contractility is increased, ventricular volume is increased, ventricular pressure is increased, etc. As described herein, heart failure is a cyclic mechanism where the body tries to compensate in response to reduced cardiac output. The increase in sympathetic tone results in increase in heart rate (to maintain cardiac output), an increase in peripheral arterial resistance (to maintain blood pressure), etc., and also an increase in MVO2 (to meet the myocardial oxygen demand). Thus, an increase in MVO2 means the heart is working much harder to meet the demand. Therefore, MVO2 is important in the assessment of heart failure, and therapy that reduces MVO2 would be useful in treating heart failure.

Baroreflex therapy works to reverse the sympathetic response and results in reduced MVO2 in patients as seen in FIG. 8C. Measuring the MVO2 indicates how hard the heart is working to contract and also whether the baroreflex therapy can be deactivated or reduced or whether it should continue or be increased until MVO2 falls within an accepted range (generally 7,000-10,000 bpm*mmHg in patients with systolic blood pressure of 120 mmHg and heart rate of 65-80 bpm). As can be seen in FIG. 8C, baroreflex therapy reduced MVO2 to acceptable levels within 4 months and continued to reduce it through 13 months.

In another embodiment, the present invention may improve arterial elasticity and/or vascular compliance. Arterial compliance is determined by structural factors, such as collagen and elastin, and functional factors, such as vasoactive neurohormones. The elastic behavior of conduit arteries contributes importantly to left ventricular function and aortic flow. Increased pulse pressure, an index of the pulsatile hemodynamic load, is a risk factor for the development of congestive heart failure. The increased pulsatile load that results from a decrease in arterial compliance reduces left ventricular stroke volume more so when the contractile state is depressed than in the normally functioning ventricle. Therefore, impaired arterial elasticity is particularly deleterious in patients with congestive heart failure.

Baroreflex therapy works to improve such factors as venous reserve and capacitance, thus improving elasticity of vessels. Measuring arterial compliance by means of such measures as augmentation index, and also pulse pressure (which is an indicator of aortic stiffness) can indicate a patient's propensity for or current heart failure status. FIG. 8C depicts measurements of arterial compliance with echocardiogram and is measured in units of mL/mmHg. The normal range for patients using this measurement is approximately 1-2 mL/mmHg depending on age (as compliance generally is reduced with age). As seen in FIG. 8C, baroreflex therapy results in increased arterial compliance at 4 months and continues to 13 months. Pulse pressure is also reduced.

Arterial PV Loops for Real-Time Measurement of Heart and Arterial Function

In one embodiment, the invention provides an implantable, real-time pressure-volume loop monitoring device. Pressure-volume loops and their relationships to various mechanisms of the heart have been described since the early 1900s. For example, Starling described the relationship between filling pressure of the ventricle and stroke volume in 1914. The well known Frank-Starling mechanism describes the ability of the heart to match an increased venous return with an augmented stroke volume. PV loops are currently used for measuring pressure and volume perioperatively.

Figure 1A:
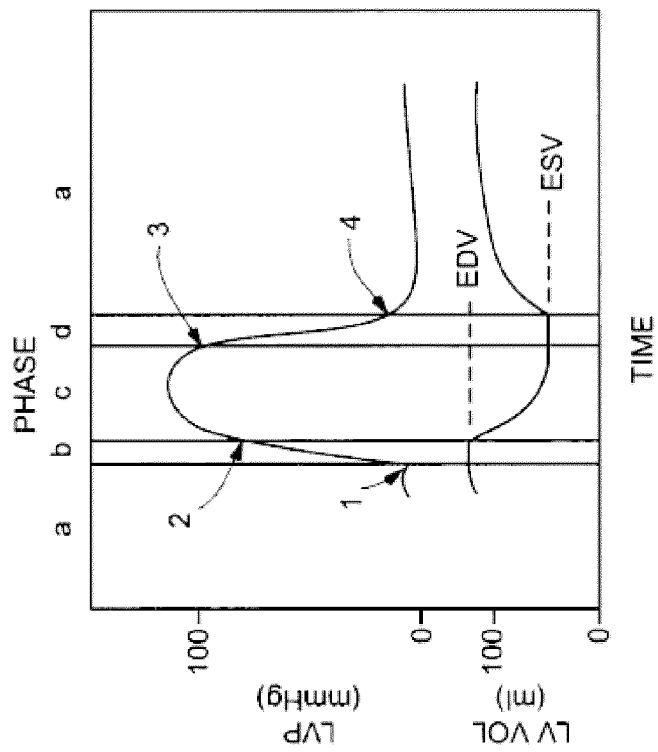
FIG. 1A is a graph of the cardiac phases.

Generally, left ventricular (LV) PV loops are derived from pressure and volume information found in a cardiac cycle diagram. To generate a PV loop for the left ventricle, the left ventricular pressure (LVP) is plotted against LV volume at multiple time points during a complete cardiac cycle. Various parameters related to cardiac function can be derived from LV loops. For example, parameters related to information such as ventricular filling, contraction, ejection, relaxation, end diastolic volume and end diastolic pressure can be obtained from PV loops and are known in the art. FIGS. 1A and 1B illustrate the cardiac phases and a typical PV loop, wherein 1 corresponds to the mitral valve closing, 2 corresponds to the aortic valve opening, 3 corresponds to the aortic valve closing, and 4 corresponds to the mitral valve opening. Further, a corresponds to diastolic filling, b corresponds to isovolumetric contraction, c corresponds to ejection, and d corresponds to isovolumetric relaxation.

In this embodiment, the left ventricular end-systolic pressure and stroke volume are measured and assessed continuously or as needed by a physician. In one embodiment, the system and methods of the invention provide a device that stimulates a baroreflex in order to reduce left ventricular pressure and increase left ventricular volume. In one embodiment, the device receives information from the PV loop monitor and adjusts therapy to optimize the result.

In one embodiment, the pressure portion of the PV loop is derived from a transarterial pressure waveform. In one embodiment, the pressure portion is derived from an LV conductance catheter. In one embodiment, the pressure portion is derived from a pressure sensor in the aorta and the signal is obtained during the systole phase of the cardiac cycle. In one embodiment, the volume portion is derived from transarterial impedance waveform, which is derived from a flow measurement. In another embodiment, a separate sensor capable of determining blood flow is provided, and is used to generate the volume portion of the PV loop. In one embodiment reduced left ventricular pressure is confirmed by the implanted, real time, continuous PV loop of the invention. In one embodiment, the increased left ventricular volume is confirmed by the implanted, real time, continuous PV loop of the invention.

At least a portion of the PV loop can be generated from an impedance measurement on the aorta. During systole, the aortic valve is open, such that the pressure in the aorta the same as the pressure in the left ventricle. The impedance of the aorta is measured, and a pressure waveform is generated from the measured impedance values. In one embodiment, the pressure waveform may be processed to obtain a value indicative of flow, which can be integrated over time to obtain volume. From these values, the "top" portion of an LV loop (corresponding to systole) can be generated.

Figures 9A, 9B:
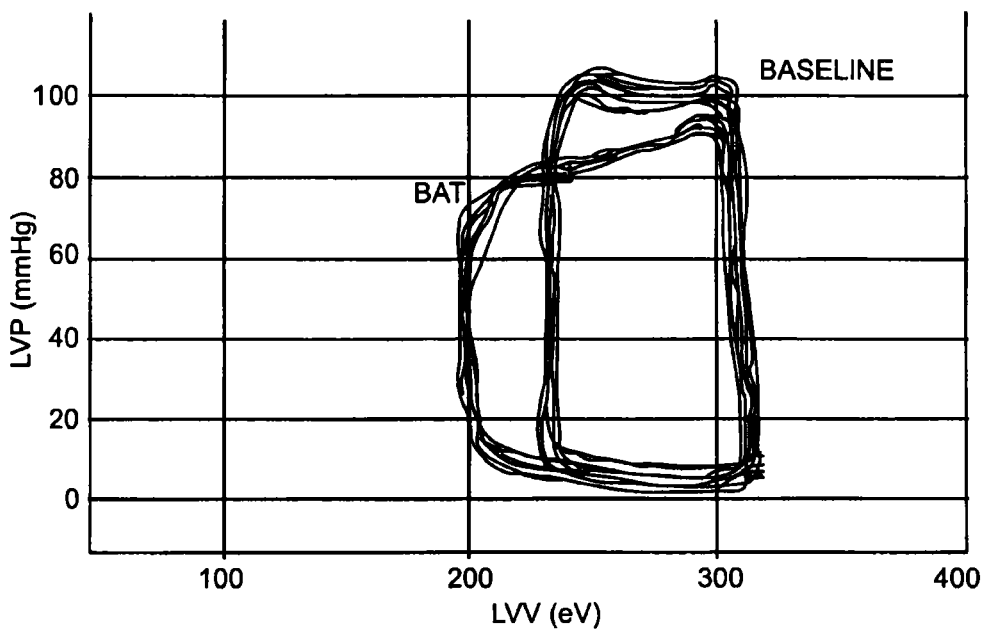
FIG. 9A is a graph depicting a PV loop before and after application of a baroreflex therapy according to an embodiment of the present invention.
FIG. 9B is a table depicting patient physiological parameters following application of a baroreflex therapy according to an embodiment of the present invention.
Figures 10A, 10B:
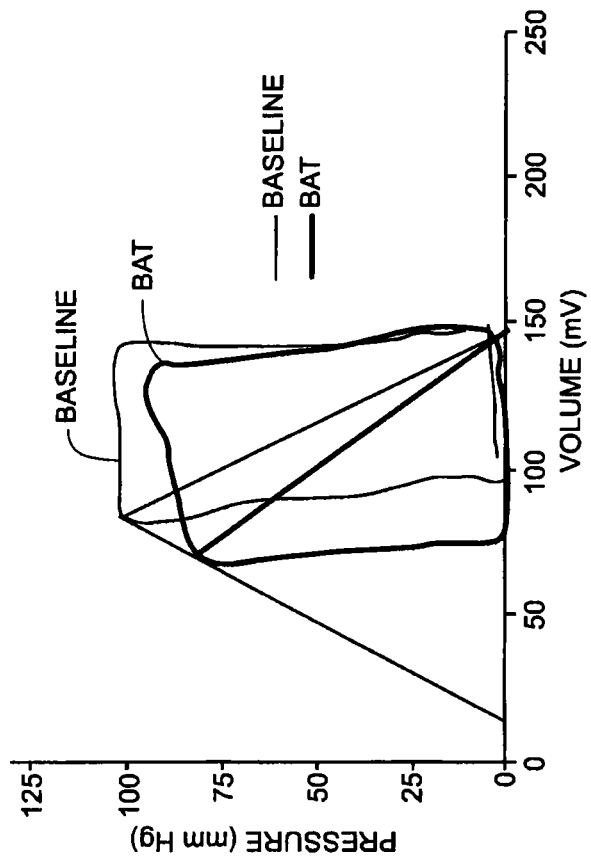
FIG. 10A is a graph depicting a PV loop before and after application of a baroreflex therapy according to an embodiment of the present invention.
FIG. 10B is a table depicting patient physiological parameters following application of a baroreflex therapy according to an embodiment of the present invention.

To demonstrate efficacy of baroreflex activation therapy effects on hemodynamic measures, experiments were performed on canines FIGS. 9A-10B depicts the reduction in LV pressure and increase in LV volume after BAT; FIG. 10B illustrates the hemodynamic characteristics. Referring specifically to FIG. 9A, the PV loop illustrates lower arterial pressures and increased stroke volumes following BAT. FIG. 9B illustrates that in a normal canine subject, application of baroreflex activation therapy reduces heart rate, reduces cardiac load (pressures), and slightly reduces the speed with which the heart contracts (dpdt). Reduced fatigue and improved coronary perfusion should occur in a patient that has received baroreflex activation therapy.

Referring to FIGS. 10A-10B, a reduction in heart rate and an increase in each of stroke volume, ejection fraction, and cardiac output can be seen following application of baroreflex activation therapy. Further, a reduction in Tau (time constant of LV relaxation) and an increase in peak filling rate indicate improved diastolic function. The rate-pressure-product (RPP) decrease indicates the heart is consuming less energy, despite the increased cardiac output.

Combined Baroreflex Therapy and Vagal Nerve Stimulation

In one embodiment, the invention comprises a system that improves the normalization of sympathetic/parasympathetic balance by combining baroreflex activation therapy with a vagal nerve electrode that provides efferent vagal nerve stimulation to the heart for more precise and robust heart rate control, or provides a stimulus to inhibit efferent vagal nerve activity to the heart if heart rate drops too low with baroreflex activation therapy. The advantages of this therapy for heart failure are that vagal nerve stimulation alone lowers heart rate but does not affect the vasculature. Current baroreflex activation therapy affects both heart rate and the vasculature but does not provide selective control of heart rate and blood pressure and may be perceived to cause precipitous drops in arterial pressure in certain heart failure patients. By providing an additional mechanism to augment the heart rate drop, this invention allows for greater heart rate and pressure control than either system alone.

The parasympathetic nervous system has a complementary relationship with the sympathetic nervous system. The body uses these two systems to regulate blood pressure. Stimulation or enhancement of the parasympathetic nervous system generally causes a decrease in blood pressure. Stimulating or enhancing the sympathetic nervous system, on the other hand, generally causes blood pressure to increase. If cardiac output is insufficient to meet demand (i.e., the heart is unable to pump sufficient blood), the brain activates a number of body systems, including the heart, kidneys, blood vessels, and other organs/tissues to correct this.

In one embodiment, baroreflex activation therapy is achieved by electrodes placed around the carotid sinus, and vagal nerve stimulation is achieved by an electrode placed around the right vagus nerve. In other embodiments, vagal nerve stimulation is achieved by an electrode placed intravascularly, for example either in the jugular vein for stimulating the right vagus nerve, or in the superior vena cava to stimulate the cardiac branches of the vagus nerve. Using sensors for monitoring heart rate and blood pressure, the combined system alters baroreflex activation therapy intensity and vagal nerve stimulation intensity to achieve target heart rate reductions without compromising blood pressure. For example, if the heart rate target has not been achieved with baroreflex activation therapy, but the blood pressure target value has been achieved, vagal nerve stimulation is applied to reduce heart rate further.

The system is also programmable to alter intensities of baroreflex activation therapy and vagal nerve stimulation to achieve target blood pressures and heart rates in a more efficient manner than baroreflex activation therapy or vagal nerve stimulation alone. For example, when high intensity baroreflex activation therapy is required to achieve target heart rate but blood pressure is not too low, the system operates in a closed-loop fashion to reduce intensity of baroreflex activation therapy as much as possible, without losing any of the pressure response, while increasing vagal nerve stimulation to account for any loss of heart rate response. The system uses an algorithm to monitor blood pressure, heart rate, baroreflex activation therapy intensity, and vagal nerve stimulation intensity, to find the most efficient combination of baroreflex activation therapy and vagal nerve stimulation intensities to achieve target blood pressure and heart rate values. In the event that the baroreflex activation therapy intensity required for achieving a target pressure response causes heart rate to drop too far, the system inhibits efferent vagal nerve activity by providing vagal nerve stimulation to inhibit nerve traffic in the efferent direction, thereby counteracting the parasympathetic activity enhancement by baroreflex activation therapy.

Baroreceptor signals in the arterial vasculature are used to activate a number of body systems which collectively may be referred to as the baroreflex system. For the purposes of the present invention, it will be assumed that the "receptors" in the venous and cardiopulmonary vasculature (including the pulmonary artery) and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, the present invention may activate baroreceptors, mechanoreceptors, pressoreceptors, stretch receptors, chemoreceptors, or any other venous, heart, or cardiopulmonary receptors which affect the blood pressure, nervous system activity, and neurohormonal activity in a manner analogous to baroreceptors in the arterial vasculation. For convenience, all such venous receptors will be referred to collectively herein as "baroreceptors" or "receptors" unless otherwise expressly noted.

While there may be small structural or anatomical differences among various receptors in the vasculature, for the purposes of some embodiments of the present invention, activation may be directed at any of these receptors and/or nerves and/or nerve endings from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. Stimulation of the baroreflex system may be accomplished by stimulating such receptors, nerves, nerve fibers, or nerve endings, or any combination thereof.

Arrhythmias

A study was performed examining the effects of baroreflex activation therapy on the induction of ventricular tachycardia or ventricular fibrillation in canines with intracoronary microembolization-induced advanced heart failure (LV ejection fraction ~20%). Canines with heart failure underwent programmed ventricular stimulation performed from the right ventricular apex. Stimulation parameters of the baroreflex therapy system were chosen for each subject in order to achieve a desired level of baroreflex activation therapy, measured as an approximate 10-20% drop in arterial pressure under anesthesia (1% isofluorane). Devices were then programmed to these stimulation parameters at the beginning of the therapy period and remained at these settings throughout the three month therapy period.

Figure 11:
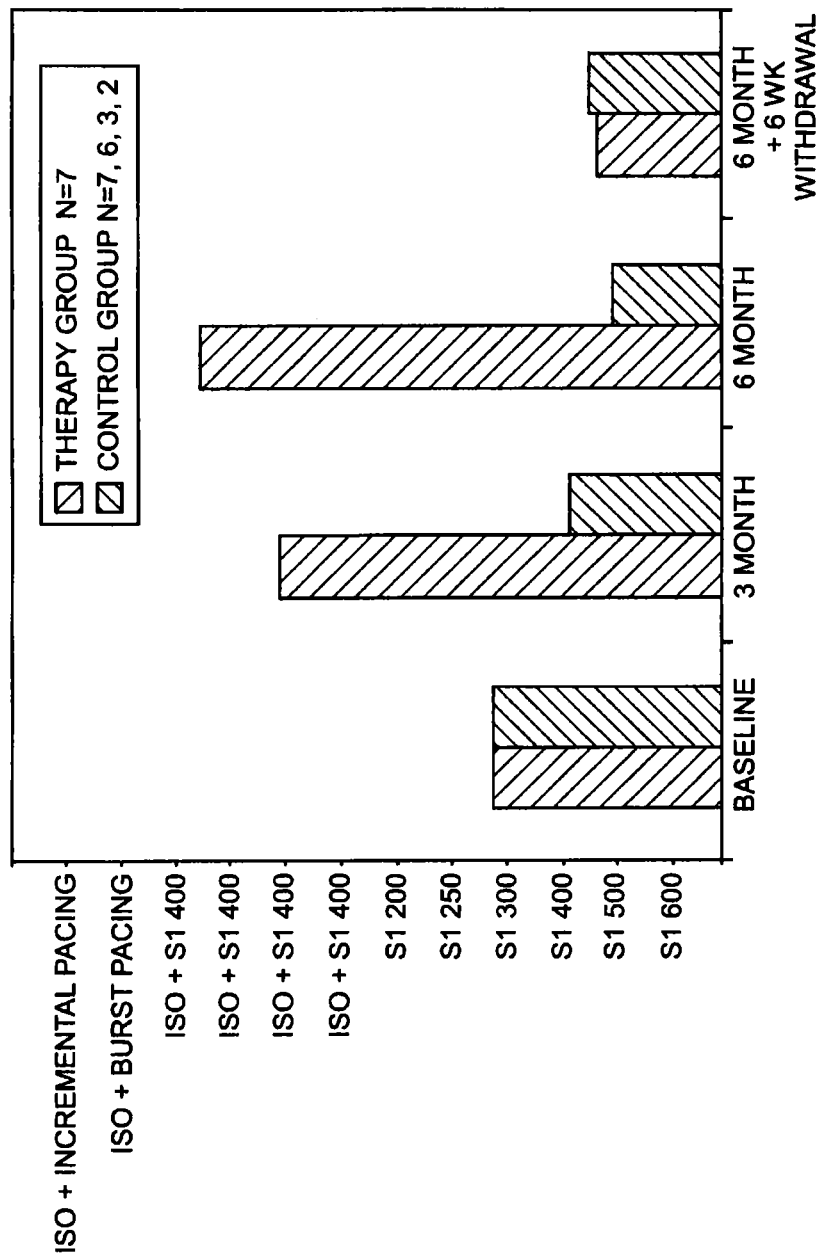
FIG. 11 is a chart depicting patient physiological parameters following application of a baroreflex therapy according to an embodiment of the present invention.

The results in FIG. 11 show that in addition to improving LV function and attenuating LV remodeling, long-term baroreflex activation therapy reduces the incidence of inducible lethal ventricular arrhythmias in canine patients with chronic advanced heart failure. This added benefit of baroreflex activation therapy provides further support for the use of this novel approach for the treatment of chronic heart failure.

CRT Therapy

In one embodiment, the pressure waveform is generated with information from a sensor located in for example an artery and used to input to a cardiac resynchronization therapy (CRT) device. In this embodiment, the CRT pulse is adjusted based on the measured time and/or amplitude variables obtained from the waveform. In one embodiment, the CRT programming adjustment can be made manually by for example a physician. In one embodiment, the pressure sensor is connected to the CRT therapy device and programming can be done automatically by the CRT device. In one embodiment, the device determines if the CRT therapy is working and adjusts the baroreflex activation therapy accordingly. For example, the device may use information for the derived pressure waveform and determine if the CRT is improving for example the reflected wave. If it is not, baroreflex activation therapy is applied until a desired reflected wave modification is seen.

Norepinephrine and Angiotensin II:

In one embodiment, a closed-loop system monitors circulating markers indicative of heart failure or ensuing heart failure. Possible markers could include but are not limited to norepinephrine, angiotensin II, aldosterone or BNP. Other known markers in the art could be used. In one embodiment, the HF marker monitoring system is used in combination with the baroreflex activation therapy system to monitor and adjust therapy in order to optimize efficacy and efficiency of the device.

Figure 12:
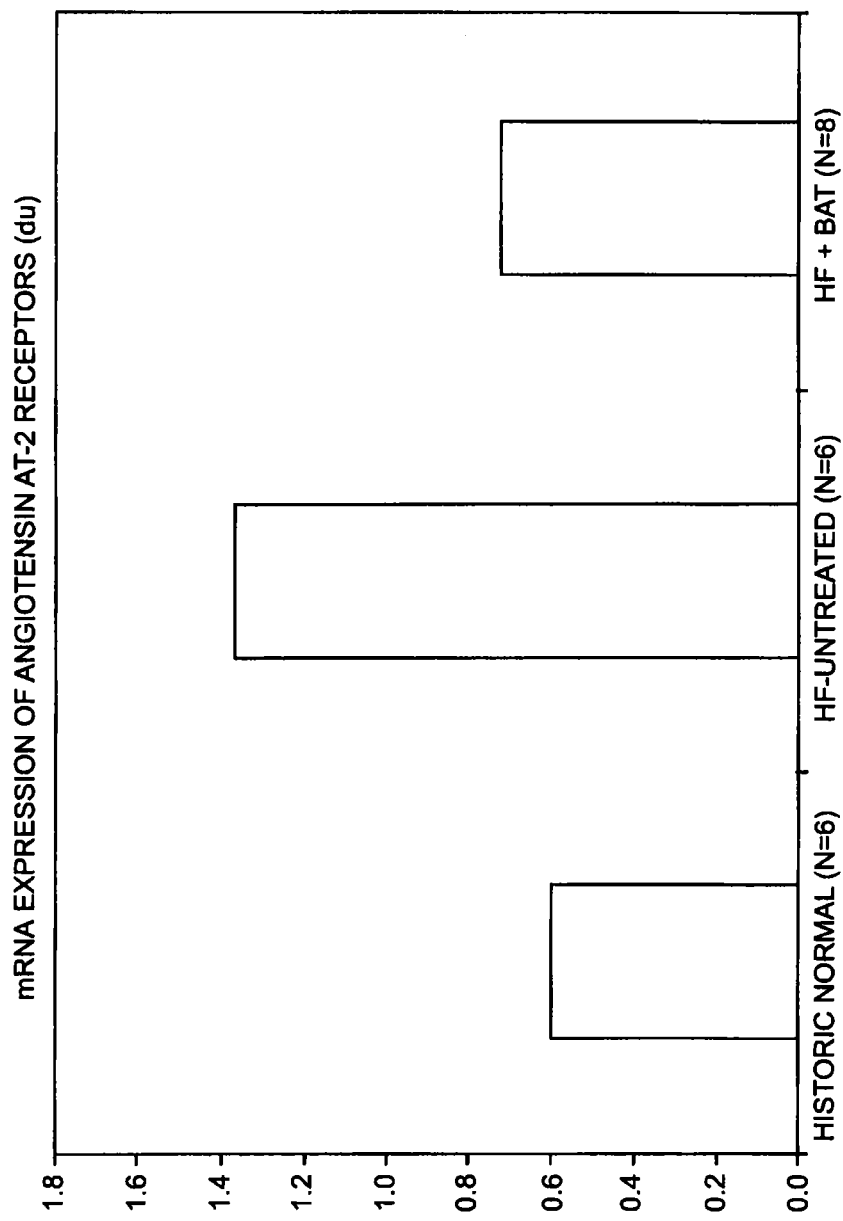
FIG. 12 is a chart depicting levels of markers indicative of heart failure before and after application of a baroreflex therapy according to an embodiment of the present invention.
Figure 13:
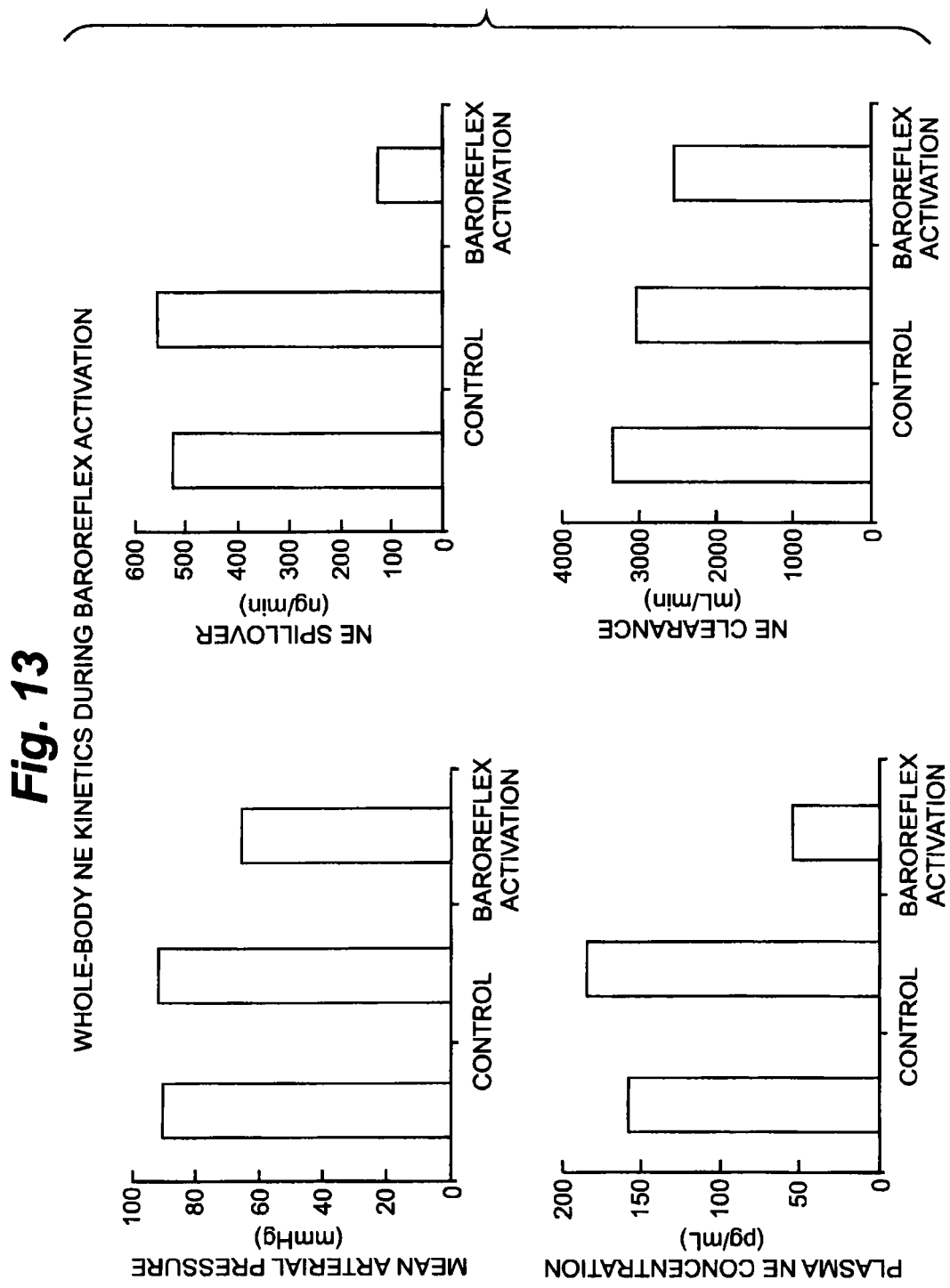
FIG. 13 is a group of charts depicting physiological parameters of control subjects compared to subjects that have received baroreflex therapy according to an embodiment of the present invention.

To prove efficacy of baroreflex activation therapy to reduce markers indicative of heart failure, studies were performed to measure norepinephrine (NE) and angiotensin II (ANG) plasma levels before and after baroreflex activation therapy in dogs with HF. Results indicate that baroreflex activation therapy of the carotid sinus delays the increase in plasma NE and ANG II and significantly enhances survival in dogs with pacing-induced HF. Chronic baroreflex activation therapy reduces renal vasoconstriction during exercise in dogs with pacing-induced HF. These data suggest that baroreflex activation therapy may be of benefit in the treatment of severe heart failure. FIGS. 12 and 13 depict the results of three separate experiments. FIG. 12 depicts mRNA expression of Angiotensin AT-2 Receptors (du) in dogs. FIG. 13 depicts the results of whole body NE kinetics during baroreflex activation therapy, including mean arterial pressure, plasma NE levels, NE spillover and NE clearance.

Accounting for Changes in Atmospheric Pressure

In a clinical setting, blood pressure is measured with a sphygmomanometer, an inflatable cuff placed externally around the upper arm of a patient. The cuff is connected to a mercury manometer, which displays pressure values relative to atmospheric pressure. For instance, if the arterial pressure indicated by the manometer is 100 mmHg on a day when the atmospheric pressure is 760 mmHg, then the relative arterial pressure is 100 mmHg while the absolute arterial pressure is 860 mmHg. Internal blood pressure sensors must also take into account atmospheric pressure, and typically rely on an external reference.

In one embodiment, the present invention can distinguish true changes in blood pressure from changes due to fluctuations in atmospheric pressure. Blood pressure may be measured, such as with an implanted pressure transducer, and additional parameters such as heart rate and arterial properties (e.g., stiffness) are simultaneously monitored. Arterial properties may be determined from an arterial impedance measurement, as discussed above. By monitoring blood pressure, heart rate and arterial properties such as stiffness as part of a therapy, an implantable device may be able to distinguish a true change in arterial blood pressure of a patient from a change in pressure due to atmospheric pressure. For example, if blood pressure as measured by a blood pressure sensor increases, but heart rate and arterial stiffness do not, this can be indicative of an increase in atmospheric pressure and baroreflex therapy need not be administered by the device (or modulated, if therapy is already being delivered). However, if blood pressure as measured by the blood pressure sensor increases, and heart rate and arterial stiffness also increase, this is indicative of an actual increase in blood pressure that may require initiation or modification of baroreflex therapy. In this way, baroreflex therapy delivery can be modulated based on a blood pressure measurement without an external reference measurement.

The implantable device may be programmed with predetermined ranges and/or thresholds for each monitored parameter that may be used in controlling therapy. For example, ranges may be established for each of blood pressure, heart rate and arterial stiffness such that a first therapy is provided when one or more measured parameters is within its respective range, while a second therapy is provided when one or more measured parameters is outside of the range and/or reaches a predetermined threshold and/or is otherwise indicative of a need to apply or modify therapy.

Each of the first and second therapies may comprise activating, deactivating, initiating, terminating, or otherwise modifying or modulating therapy. Modulating therapy may comprise modulating one or more characteristics of the therapy, such as but not limited to amplitude, frequency, pulse width, duration, or power level.

Figure 17:
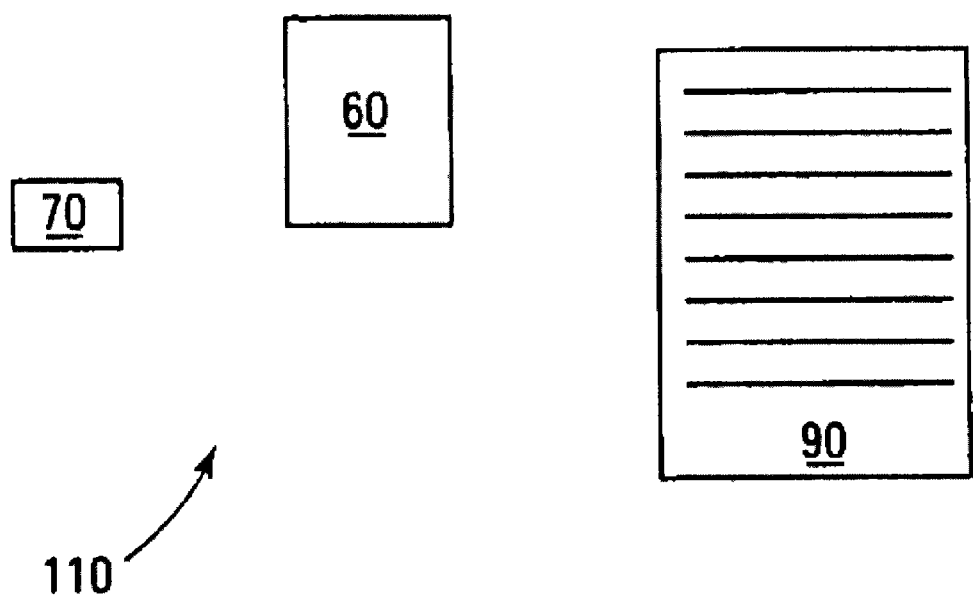
FIG. 17 is a schematic diagram of a baroreflex therapy kit in accordance with the present invention.

In one embodiment, instructions for implanting a measurement system and/or therapy system in accordance with the various embodiments described herein in the form of printed or electronically, optically or magnetically stored information to be displayed, for example, are provided as part of a kit or assemblage of items prior to surgical implantation of the system. Referring to FIG. 17, in one embodiment a baroreflex therapy system can be provided to a user in a kit 110. Kit 110 may include a baroreflex modulation device 70 having one or more electrodes, a control system 60 operably coupleable to the baroreflex modulation device 70, and a set of instructions 90 recorded on a tangible medium for operating the system. Baroreflex modulation device 70 may be configured to conduct impedance measurements, or operably coupled to a set of measurement electrodes provided as part of kit 110. Kit 110 may be comprised of one or more hermetically sealed and sterilized packages. Instructions 90 may be provided as part of kit 110 or indications may be provided linking a user to electrically accessible instructions 90. In another embodiment, instructions for implanting the system in accordance with the various embodiments described herein are provided, for example, by a manufacturer or supplier of system, separately from providing the system, such as by way of information that is accessible using the Internet or by way of seminars, lectures, training sessions or the like.

Various modifications to the embodiments of the inventions may be apparent to one of skill in the art upon reading this disclosure. For example, persons of ordinary skill in the relevant art will recognize that the various features described for the different embodiments of the inventions can be suitably combined, un-combined, and re-combined with other features, alone, or in different combinations, within the spirit of the invention. Likewise, the various features described above should all be regarded as example embodiments, rather than limitations to the scope or spirit of the inventions. Therefore, the above is not contemplated to limit the scope of the present inventions.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the present inventions, it is expressly intended that the provisions of Section 112, sixth paragraph of 35 U.S.C. are not to be invoked unless the specific terms "means for" or "step for" are recited in a claim.

The invention claimed is:

1. An implantable baroreflex system, comprising:
   a baroreflex activation device configured to be implantable proximate a blood vessel of a patient;
   a measurement device configured to be implantable proximate a blood vessel; and
   a control system coupled to the baroreflex activation device and the measurement device, and in communication with a blood pressure sensing means, the control system programmed to automatically:
      determine an impedance of the blood vessel with the measurement device;
      determine waveform data based on the blood vessel impedance over a time period of at least a portion of one cardiac cycle;
      determine a patient physiological parameter based on the waveform data; and
      compare the patient physiological parameter to a blood pressure measurement taken from the blood pressure sensing means.

2. The system of claim 1, wherein the baroreflex activation device comprises an electrode.

3. The system of claim 1, wherein the measurement device comprises an electrode.

4. The system of claim 1, wherein the measurement device is integrated with the baroreflex activation device.

5. The system of claim 1, wherein the measurement device comprises an implantable pressure transducer.

6. The system of claim 1, wherein the blood pressure sensing means is implantable within the patient and coupled to the control system.

7. The system of claim 1, wherein the blood pressure sensing means comprises an implantable blood pressure sensor.

8. The system of claim 1, wherein the blood pressure sensing means comprises a sphygmomanometer.

9. The system of claim 1, wherein the patient physiological parameter comprises blood pressure.

10. The system of claim 1, wherein the patient physiological parameter comprises heart rate.

11. The system of claim 1, wherein the patient physiological parameter comprises one of vascular stiffness, or augmentation index.

12. The system of claim 1, wherein the control system is further programmed to automatically activate, deactivate or otherwise modulate the baroreflex activation device to deliver a baroreflex therapy based on the comparison of the patient physiological parameter to the blood pressure measurement.

13. The system of claim 12, wherein the control system contains pre-determined ranges for each of the patient physiological parameter and blood pressure, the control system being further programmed to:
   deliver a first therapy when the patient physiological parameter and the blood pressure measurement are each within the pre-determined ranges; and
   deliver a second therapy when the patient physiological parameter and the blood pressure measurement each deviate from the pre-determined ranges.

14. The system of claim 12, wherein the control system contains pre-determined ranges for each of the patient physiological parameter and blood pressure, the control system being further programmed to:
   deliver a first therapy when the patient physiological parameter is within the pre-determined range and the blood pressure measurement exceeds the pre-determined range; and
   deliver a second therapy when the patient physiological parameter and the blood pressure measurement each deviate from the pre-determined ranges.

15. The system of claim 1, further comprising a heart rate sensing means in communication with the control system, the control system being further programmed to automatically compare the patient physiological parameter to a heart rate obtained from the heart rate sensing means.

16. The system of claim 15, wherein the control system contains pre-determined ranges for each of the patient physiological parameter, blood pressure, and heart rate, the control system being further programmed to:
   deliver a first therapy when the patient physiological parameter and/or heart rate are within their pre-determined ranges and the blood pressure deviates from the pre-determined range; and
   deliver a second therapy when at least one of the patient physiological parameter or heart rate deviates from their pre-determined ranges.

17. The implantable baroreflex system of claim 1, wherein the baroreflex activation device comprises a therapy electrode configured to be implantable in contact with a wall of the blood vessel, and wherein the measurement device comprises a measurement electrode configured to be implantable in contact with the wall of the blood vessel and proximate the baroreflex activation device.

18. A method, comprising:
   causing a baroreflex therapy system to be manufactured and made available to a user, wherein manufacture of the baroreflex therapy system further comprise: constructing a baroreflex activation device, constructing a measurement device, and constructing a control system coupled to the baroreflex activation device and the measurement device;
   causing a blood pressure sensing means to be manufactured and made available to a user, the blood pressure sensing means in communication with the control system; and
   providing instructions to the user recorded on a tangible medium, the instructions comprising:
   implanting the activation device proximate a blood vessel of a patient;
   implanting the measurement device proximate a blood vessel; and
   causing the control system to:
      determine an impedance of the blood vessel with the measurement device;
      determine waveform data based on the blood vessel cycle;
      determine a patient physiological parameter based on the waveform data;
      obtain a blood pressure measurement via the blood pressure sensing means; and
      compare the blood pressure measurement to the patient physiological parameter.

19. The method of claim 18, wherein the instructions further include causing the control system to activate, deactivate or otherwise modulate the baroreflex therapy system to deliver a baroreflex therapy via the baroreflex activation device based on the comparison of the patient physiological parameter to the blood pressure measurement.

20. The method of claim 19, wherein the control system contains pre-determined ranges for each of the patient physiological parameter and blood pressure, the instructions further comprising causing the control system to:
deliver a first therapy when the patient physiological parameter and the blood pressure measurement are each within the pre-determined ranges; and
deliver a second therapy when the patient physiological parameter and the blood pressure measurement each deviate from the pre-determined ranges.

21. The method of claim 19, wherein the control system contains pre-determined ranges for each of the patient physiological parameter and blood pressure, the instructions further comprising causing the control system to:
deliver a first therapy when the patient physiological parameter is within the predetermined range and the blood pressure measurement exceeds the pre-determined range; and
deliver a second therapy when the patient physiological parameter and the blood pressure measurement each deviate from the pre-determined ranges.

22. The method of claim 18, wherein the baroreflex activation device comprises a therapy electrode and wherein the measurement device comprises a measurement electrode, the instructions further comprising:
implanting the activation device such that the therapy electrode is in contact with a wall of the blood vessel; and
implanting the measurement device such that the electrode is in contact with the wall of the blood vessel and proximate the therapy electrode.

23. The method of claim 18, the instructions further comprising:
implanting at least one of the activation device and the measurement device proximate a blood vessel of a patient selected from the group consisting of: a carotid sinus, an aortic arch, a common carotid artery, a subclavian artery, a brachiocephalic artery, pulmonary artery, pulmonary vein, jugular vein, femoral artery, femoral vein, and a heart.

24. A method of comparing parameters, comprising:
providing an implantable baroreflex therapy system, including a baroreflex activation device having a therapy electrode, a measurement device having a measurement electrode, and a control system coupled to the baroreflex activation device and the measurement device;
providing a blood pressure sensing means in communication with the control system; and
implanting the baroreflex therapy system such that the therapy electrode is proximate a blood vessel of a patient and the measurement electrode is proximate the blood vessel,
wherein the control system is programmed to:
determine an impedance of the blood vessel with the implantable measurement device over a time period of at least one cardiac cycle;
determine a patient physiological parameter based on the impedance of the blood vessel;
obtain a blood pressure measurement via the blood pressure sensing means; and
compare the blood pressure measurement to the patient physiological parameter.

25. The method of claim 24, wherein the control system is further programmed to activate, deactivate or otherwise modulate the baroreflex therapy system to deliver a baroreflex therapy via the baroreflex activation device based on the comparison of the patient physiological parameter to the blood pressure measurement.

26. The method of claim 25, wherein the control system contains pre-determined ranges for each of blood pressure, heart rate and arterial stiffness, the method further comprising:
delivering a first therapy when the patient physiological parameter and the blood pressure measurement are each within the pre-determined ranges; and
delivering a second therapy when the patient physiological parameter and the blood pressure measurement each exceed the pre-determined ranges.

27. The method of claim 25, wherein the control system contains pre-determined ranges for each of blood pressure, heart rate and arterial stiffness, the method further comprising:
delivering a first therapy when the patient physiological parameter is within the predetermined range and the blood pressure measurement exceeds the pre-determined range; and
delivering a second therapy when the patient physiological parameter and the blood pressure measurement each exceed the pre-determined ranges.

28. The method of claim 24, further comprising:
implanting the baroreflex activation device such that the therapy electrode is in contact with a wall of the blood vessel; and
implanting the measurement device such that the measurement electrode is in contact with the wall of the blood vessel and proximate the therapy electrode.

29. The method of claim 24, further comprising implanting at least one of the baroreflex therapy system and the measurement device proximate a blood vessel of a patient selected from the group consisting of: a carotid sinus, an aortic arch, a common carotid artery, a subclavian artery, a brachiocephalic artery, pulmonary artery, pulmonary vein, jugular vein, femoral artery, femoral vein, and a heart.

* * * * *